(12) United States Patent
Bleich Kimelman et al.

(10) Patent No.: US 12,097,292 B2
(45) Date of Patent: *Sep. 24, 2024

(54) PROCESS FOR PREPARING MICROPARTICLES CONTAINING GLATIRAMER ACETATE

(71) Applicant: MAPI PHARMA LTD., Ness Ziona (IL)

(72) Inventors: Nadav Bleich Kimelman, Tel Aviv (IL); Shai Rubnov, Tel Aviv (IL); Ehud Marom, Tel Aviv (IL)

(73) Assignee: MAPI PHARMA LTD., Ness Ziona (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/902,030

(22) Filed: Sep. 2, 2022

(65) Prior Publication Data

US 2023/0000782 A1 Jan. 5, 2023

Related U.S. Application Data

(63) Continuation of application No. 16/328,572, filed as application No. PCT/IL2017/050954 on Aug. 28, 2017, now Pat. No. 11,471,421, application No. 17/902,030 is a continuation of application No. 16/328,582, filed as application No. PCT/IL2017/050882 on Aug. 9, 2017.

(60) Provisional application No. 62/380,426, filed on Aug. 28, 2016, provisional application No. 62/381,598, filed on Aug. 31, 2016.

(51) Int. Cl.
*A61K 9/00* (2006.01)
*A61K 9/19* (2006.01)
*A61K 9/50* (2006.01)

(52) U.S. Cl.
CPC .......... *A61K 9/5094* (2013.01); *A61K 9/0019* (2013.01); *A61K 9/19* (2013.01); *A61K 9/5031* (2013.01)

(58) Field of Classification Search
CPC ...... A61K 9/5094; A61K 9/0019; A61K 9/19; A61K 9/5031
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,773,919 A | 11/1973 | Boswell |
| 3,845,770 A | 11/1974 | Theeuwes |
| 3,849,550 A | 11/1974 | Teitelbaum |
| 3,916,899 A | 11/1975 | Theeuwes |
| 4,008,719 A | 2/1977 | Theeuwes |
| 4,822,340 A | 4/1989 | Kamstra |
| 5,059,595 A | 10/1991 | Le Grazie |
| 5,073,543 A | 12/1991 | Marshall |
| 5,120,548 A | 6/1992 | McClelland |
| 5,354,556 A | 10/1994 | Sparks |
| 5,578,442 A | 11/1996 | Desai |
| 5,591,767 A | 1/1997 | Mohr |
| 5,639,476 A | 6/1997 | Oshlack |
| 5,643,605 A | 7/1997 | Cleland |
| 5,674,533 A | 10/1997 | Santus |
| 5,733,559 A | 3/1998 | Citernesi |
| 5,792,477 A | 8/1998 | Rickey |
| 5,800,808 A | 9/1998 | Konfino |
| 5,858,964 A | 1/1999 | Aharoni |
| 5,945,126 A | 8/1999 | Thanoo |
| 5,981,589 A | 11/1999 | Konfino |
| 6,048,898 A | 4/2000 | Konfino |
| 6,054,430 A | 4/2000 | Eliezer |
| 6,214,791 B1 | 4/2001 | Arnon |
| 6,309,669 B1 | 10/2001 | Setterstrom |
| 6,342,476 B1 | 1/2002 | Konfino |
| 6,362,161 B1 | 3/2002 | Konfino |
| 6,448,225 B2 | 9/2002 | O'Connor |
| 6,454,746 B1 | 9/2002 | Bydlon |
| 6,506,410 B1 | 1/2003 | Park |
| 6,514,938 B1 | 2/2003 | Gad |
| 6,596,316 B2 | 7/2003 | Lyons |
| 6,620,847 B2 | 9/2003 | Konfino |
| 6,800,285 B2 | 10/2004 | Rodriguez |
| 6,800,287 B2 | 10/2004 | Gad |

(Continued)

FOREIGN PATENT DOCUMENTS

AU 2013203367 B2 6/2015
CA 2020477 C 11/2000

(Continued)

OTHER PUBLICATIONS

Grodowska et al., Acta Poloniae Pharmaceutica—Drug Research, vol. 67 No. 1 pp. 3-12, 2010. (Year: 2010).*
Polman et al., (2005) Diagnostic criteria for multiple sclerosis: 2005 revisions to the "McDonald Criteria". Ann Neurol 58(6): 840-846.
Prescribing Information, EMD Serono, Rebif Prescribing Information (Sep. 2009), Novartis Pharmaceuticals Corporation, 25 pages.
Prescribing Information, Extavia (Interferon beta-1b) Kit for subcutaneous use Highlights of Prescribing Information (Aug. 2009) (on file with author), Novartis Pharmaceuticals Corporation, 3 pages.
Press Release, Biogen Idec, Inc., Avonex® (Interferon beta-1a) IM Injection (Oct. 2008) (on file with author), Biogen Idec Inc., 27 pages.

(Continued)

*Primary Examiner* — Robert S Cabral
(74) *Attorney, Agent, or Firm* — ROTHWELL, FIGG, ERNST & MANBECK, P.C.

(57) ABSTRACT

The present invention provides an improved process for preparing microparticles containing glatiramer acetate having low levels of residual organic solvent(s), in particular dichloromethane. The microparticles are incorporated into long acting parenteral pharmaceutical compositions in depot form that are suitable for subcutaneous or intramuscular implantation or injection, and that may be used to treat multiple sclerosis.

20 Claims, No Drawings

(56) References Cited

U.S. PATENT DOCUMENTS

| | | |
|---|---|---|
| 6,835,711 B2 | 12/2004 | Eisenbach-Schwartz |
| 6,844,314 B2 | 1/2005 | Eisenbach-Schwartz |
| 6,861,064 B1 | 3/2005 | Laakso |
| 6,939,539 B2 | 9/2005 | Konfino |
| 7,022,663 B2 | 4/2006 | Gilbert |
| 7,033,582 B2 | 4/2006 | Yong |
| 7,074,580 B2 | 7/2006 | Gad |
| 7,163,802 B2 | 1/2007 | Gad |
| 7,195,778 B2 | 3/2007 | Fleshner-Barak |
| 7,199,098 B2 | 4/2007 | Konfino |
| 7,230,085 B2 | 6/2007 | Griffiths |
| 7,279,172 B2 | 10/2007 | Aharoni |
| 7,342,033 B2 | 3/2008 | Polman |
| 7,351,686 B2 | 4/2008 | Eisenbach-Schwartz |
| 7,381,790 B2 | 6/2008 | Strominger |
| 7,425,332 B2 | 9/2008 | Sela |
| 7,429,374 B2 | 9/2008 | Klinger |
| 7,495,072 B2 | 2/2009 | Dolitzky |
| 7,560,100 B2 | 7/2009 | Pinchasi |
| 7,576,051 B2 | 8/2009 | Kurokawa |
| 7,615,359 B2 | 11/2009 | Gad |
| 7,625,861 B2 | 12/2009 | Konfino |
| 7,635,695 B2 | 12/2009 | Burkitt |
| 7,655,221 B2 | 2/2010 | Rasmussen |
| 7,834,039 B2 | 11/2010 | Hobson |
| 7,855,176 B1 | 12/2010 | Altman |
| 7,923,215 B2 | 4/2011 | Klinger |
| 7,928,131 B2 | 4/2011 | Buzard |
| 7,968,511 B2 | 6/2011 | Vollmer |
| 8,008,258 B2 | 8/2011 | Aharoni |
| 8,138,201 B2 | 3/2012 | Kalafer |
| 8,232,250 B2 | 7/2012 | Klinger |
| 8,236,778 B2 | 8/2012 | Avila Zaragoza |
| 8,367,605 B2 | 2/2013 | Konfino |
| 8,377,885 B2 | 2/2013 | Marom |
| 8,389,228 B2 | 3/2013 | Klinger |
| 8,389,479 B2 | 3/2013 | Gelder |
| 8,394,763 B2 | 3/2013 | Forte |
| 8,399,211 B2 | 3/2013 | Gad |
| 8,399,413 B2 | 3/2013 | Klinger |
| 8,410,115 B2 | 4/2013 | Lieberburg |
| 8,440,622 B2 | 5/2013 | Stossel |
| 8,709,433 B2 | 4/2014 | Kasper |
| 8,759,302 B2 | 6/2014 | Dhib-Jalbut |
| 8,796,226 B2 | 8/2014 | Marom |
| 8,815,511 B2 | 8/2014 | Tchelet |
| 8,828,668 B2 | 9/2014 | Axtell |
| 8,920,373 B2 | 12/2014 | Altman |
| 8,969,302 B2 | 3/2015 | Klinger |
| 9,018,170 B2 | 4/2015 | Altman |
| 9,109,006 B2 | 8/2015 | Srinivasan |
| 9,114,136 B2 | 8/2015 | Kalafer |
| 9,155,775 B1 | 10/2015 | Cohen |
| 9,155,776 B2 | 10/2015 | Klinger |
| 9,200,114 B2 | 12/2015 | Marom |
| 9,402,874 B2 | 8/2016 | Klinger |
| 9,452,175 B2 | 9/2016 | Voskuhl |
| 9,702,007 B2 | 7/2017 | Tchelet |
| 10,493,122 B2 | 12/2019 | Sela |
| 2001/0007758 A1 | 7/2001 | Weiner |
| 2002/0037848 A1 | 3/2002 | Eisenbach-Schwartz |
| 2002/0077278 A1 | 6/2002 | Yong |
| 2002/0137681 A1 | 9/2002 | Steinman |
| 2003/0092059 A1 | 5/2003 | Salfeld |
| 2003/0104048 A1 | 6/2003 | Patel |
| 2003/0144286 A1 | 7/2003 | Frenkel |
| 2004/0038887 A1 | 2/2004 | Strominger |
| 2004/0106554 A1 | 6/2004 | Konfino |
| 2005/0014694 A1 | 1/2005 | Yong |
| 2005/0019322 A1 | 1/2005 | Rodriguez |
| 2005/0170004 A1 | 8/2005 | Rosenberger |
| 2005/0170005 A1 | 8/2005 | Rashba-Step |
| 2005/0171286 A1 | 8/2005 | Konfino |
| 2005/0277885 A1 | 12/2005 | Scherer |
| 2006/0154862 A1 | 7/2006 | Ray |
| 2006/0172942 A1 | 8/2006 | Dolitzky |
| 2006/0189527 A1 | 8/2006 | Rasmussen |
| 2006/0194725 A1 | 8/2006 | Rasmussen |
| 2006/0240463 A1 | 10/2006 | Lancet |
| 2006/0264354 A1 | 11/2006 | Aharoni |
| 2006/0276390 A1 | 12/2006 | Aharoni |
| 2007/0021324 A1 | 1/2007 | Dolitzky |
| 2007/0021341 A1 | 1/2007 | Sela |
| 2007/0037740 A1 | 2/2007 | Pinchasi |
| 2007/0048794 A1 | 3/2007 | Gad |
| 2007/0054857 A1 | 3/2007 | Pinchasi |
| 2007/0059798 A1 | 3/2007 | Gad |
| 2007/0081976 A1 | 4/2007 | Cohen |
| 2007/0135466 A1 | 6/2007 | Ledeboer |
| 2007/0161566 A1 | 7/2007 | Pinchasi |
| 2007/0173442 A1 | 7/2007 | Vollmer |
| 2007/0244056 A1 | 10/2007 | Hayardeny |
| 2007/0248569 A1 | 10/2007 | Eisenbach-Schwartz |
| 2008/0063687 A1 | 3/2008 | Chou |
| 2008/0085269 A1 | 4/2008 | Eisenbach-Schwartz |
| 2008/0118553 A1 | 5/2008 | Frenkel |
| 2008/0194462 A1 | 8/2008 | Wucherpfennig |
| 2008/0207526 A1 | 8/2008 | Strominger |
| 2008/0248122 A1 | 10/2008 | Rashba-Step |
| 2008/0261894 A1 | 10/2008 | Kreitman |
| 2008/0279819 A1 | 11/2008 | Went |
| 2009/0010885 A1 | 1/2009 | Vandenbark |
| 2009/0048181 A1 | 2/2009 | Schipper |
| 2009/0053253 A1 | 2/2009 | Klinger |
| 2009/0060873 A1 | 3/2009 | Sporn |
| 2009/0118298 A1 | 5/2009 | George |
| 2009/0130121 A1 | 5/2009 | Arnon |
| 2009/0149541 A1 | 6/2009 | Stark |
| 2009/0191173 A1 | 7/2009 | Eisenbach-Schwartz |
| 2009/0202527 A1 | 8/2009 | Panzara |
| 2009/0237078 A1 | 9/2009 | Shriver |
| 2010/0135953 A1 | 6/2010 | Eisenbach-Schwartz |
| 2010/0160894 A1 | 6/2010 | Julian |
| 2010/0167983 A1 | 7/2010 | Kreitman |
| 2010/0210817 A1 | 8/2010 | Gad |
| 2010/0226963 A1 | 9/2010 | Cooper |
| 2010/0285600 A1 | 11/2010 | Lancet |
| 2010/0298227 A1 | 11/2010 | Aharoni |
| 2010/0305023 A1 | 12/2010 | Stark |
| 2011/0046065 A1 | 2/2011 | Klinger |
| 2011/0060279 A1 | 3/2011 | Altman |
| 2011/0066112 A1 | 3/2011 | Altman |
| 2011/0195049 A1 | 8/2011 | Deftereos |
| 2011/0268699 A1 | 11/2011 | Deftereos |
| 2012/0015891 A1 | 1/2012 | Marom |
| 2012/0027718 A1 | 2/2012 | Kreitman |
| 2012/0199516 A1 | 8/2012 | Frohna |
| 2012/0269762 A1 | 10/2012 | Pickering |
| 2012/0276048 A1 | 11/2012 | Panzara |
| 2012/0309671 A1 | 12/2012 | Klinger |
| 2013/0165387 A1 | 6/2013 | Klinger |
| 2013/0309199 A1 | 11/2013 | Irmgard |
| 2013/0330277 A1 | 12/2013 | Blight |
| 2014/0056848 A1 | 2/2014 | Mak |
| 2014/0107208 A1 | 4/2014 | Comabella |
| 2014/0135254 A1 | 5/2014 | Fetzer |
| 2014/0193827 A1 | 7/2014 | Schwartz |
| 2014/0235670 A1 | 8/2014 | Tarcic |
| 2014/0255346 A1 | 9/2014 | Kuerten |
| 2014/0271532 A1 | 9/2014 | Kreitman |
| 2014/0271630 A1 | 9/2014 | Vollmer |
| 2014/0294899 A1 | 10/2014 | Kasper |
| 2014/0322158 A1 | 10/2014 | Dhib-Jalbut |
| 2014/0348861 A1 | 11/2014 | Surolia |
| 2015/0044168 A1 | 2/2015 | Herbst |
| 2015/0045306 A1 | 2/2015 | Tchelet |
| 2015/0164977 A1 | 6/2015 | Klinger |
| 2015/0238602 A1 | 8/2015 | Cadavid |
| 2015/0359761 A1 | 12/2015 | Blitzer |
| 2016/0040236 A1 | 2/2016 | Hosur |
| 2016/0045570 A1 | 2/2016 | Bushnell |
| 2016/0213633 A1 | 7/2016 | Ladkani |
| 2016/0250172 A1 | 9/2016 | Goelz |
| 2016/0250251 A1 | 9/2016 | Klinger |

(56) References Cited

U.S. PATENT DOCUMENTS

| | | | |
|---|---|---|---|
| 2016/0347816 A1 | 12/2016 | Toporik | |
| 2017/0022276 A1 | 1/2017 | Lieberburg | |
| 2017/0029522 A1 | 2/2017 | Smith | |
| 2020/0147141 A1 | 5/2020 | Marom | |

FOREIGN PATENT DOCUMENTS

| | | | | |
|---|---|---|---|---|
| CN | 1398584 A | 2/2003 | | |
| CN | 103169670 A | 6/2013 | | |
| CN | 104349792 A | 2/2015 | | |
| EP | 1528922 B1 | 3/2006 | | |
| EP | 1261361 B1 | 6/2006 | | |
| EP | 0975351 B1 | 3/2007 | | |
| EP | 1799703 B1 | 1/2010 | | |
| EP | 2275086 B1 | 3/2012 | | |
| EP | 2500072 A1 * | 9/2012 | ........... | B01D 9/0004 |
| EP | 2405749 B1 | 5/2013 | | |
| EP | 2424513 B1 | 5/2015 | | |
| EP | 1797109 B1 | 2/2016 | | |
| EP | 2139467 B1 | 9/2016 | | |
| EP | 2949335 B1 | 1/2017 | | |
| EP | 3130349 A1 | 2/2017 | | |
| EP | 3409286 A1 | 12/2018 | | |
| JP | H01121222 A | 5/1989 | | |
| JP | 2002-500631 A | 1/2002 | | |
| JP | 2007-500693 A | 1/2007 | | |
| JP | 2007-509981 A | 4/2007 | | |
| JP | 2007-517902 A | 7/2007 | | |
| JP | 2007-531701 A | 11/2007 | | |
| JP | 2009-515999 A | 4/2009 | | |
| JP | 2016-510343 A | 4/2016 | | |
| WO | 9501096 A1 | 1/1995 | | |
| WO | 9531990 A1 | 11/1995 | | |
| WO | 97026869 A1 | 7/1997 | | |
| WO | 98030227 A1 | 7/1998 | | |
| WO | 00005249 A2 | 2/2000 | | |
| WO | 0005250 A1 | 2/2000 | | |
| WO | 00018794 A1 | 4/2000 | | |
| WO | 00020010 A1 | 4/2000 | | |
| WO | 0027417 A1 | 5/2000 | | |
| WO | 0152878 A2 | 7/2001 | | |
| WO | 01060392 A1 | 8/2001 | | |
| WO | 0193893 A2 | 12/2001 | | |
| WO | 01093828 A1 | 12/2001 | | |
| WO | 01097846 A1 | 12/2001 | | |
| WO | 03048735 A2 | 6/2003 | | |
| WO | 2004043995 A2 | 5/2004 | | |
| WO | 2004064717 A2 | 8/2004 | | |
| WO | 2004091573 A1 | 10/2004 | | |
| WO | 2004103297 A2 | 12/2004 | | |
| WO | 2005009333 A2 | 2/2005 | | |
| WO | 2005035088 A2 | 4/2005 | | |
| WO | 2005041933 A1 | 5/2005 | | |
| WO | 2005070332 A1 | 8/2005 | | |
| WO | 2005084377 A2 | 9/2005 | | |
| WO | 2005085323 A2 | 9/2005 | | |
| WO | 2005120542 A2 | 12/2005 | | |
| WO | 2006029036 A2 | 3/2006 | | |
| WO | 2006029393 A2 | 3/2006 | | |
| WO | 2006029411 A2 | 3/2006 | | |
| WO | 2006050122 A1 | 5/2006 | | |
| WO | 2006057003 A2 | 6/2006 | | |
| WO | 2006083608 A1 | 8/2006 | | |
| WO | 2006089164 A1 | 8/2006 | | |
| WO | 2006116602 A2 | 11/2006 | | |
| WO | 2007021970 A2 | 2/2007 | | |
| WO | 2007022254 A2 | 2/2007 | | |
| WO | 2007030573 A2 | 3/2007 | | |
| WO | 2007059342 A2 | 5/2007 | | |
| WO | 2007081975 A2 | 7/2007 | | |
| WO | 2008006026 A1 | 1/2008 | | |
| WO | 2008075365 A1 | 6/2008 | | |
| WO | 2009040814 A1 | 4/2009 | | |
| WO | 2009063459 A2 | 5/2009 | | |
| WO | 2009070298 A1 | 6/2009 | | |
| WO | 2010011879 A2 | 1/2010 | | |
| WO | 2010024908 A1 | 3/2010 | | |
| WO | 2011008274 A2 | 1/2011 | | |
| WO | 2011022063 A1 | 2/2011 | | |
| WO | 2011080733 A1 | 7/2011 | | |
| WO | 2012051106 A1 | 4/2012 | | |
| WO | 2012143924 A1 | 10/2012 | | |
| WO | 2013055683 A1 | 4/2013 | | |
| WO | 2013171345 A1 | 11/2013 | | |
| WO | 2014058976 A2 | 4/2014 | | |
| WO | 2014107533 A2 | 7/2014 | | |
| WO | 2014165280 A1 | 10/2014 | | |
| WO | 2015037000 A1 | 3/2015 | | |
| WO | 2015037005 A1 | 3/2015 | | |
| WO | 2015168000 A1 | 11/2015 | | |
| WO | 2016036719 A1 | 3/2016 | | |
| WO | 2016036721 A1 | 3/2016 | | |
| WO | 2016040861 A1 | 3/2016 | | |
| WO | 2016064997 A1 | 4/2016 | | |
| WO | 2016112270 A1 | 7/2016 | | |
| WO | 2016160830 A1 | 10/2016 | | |
| WO | 2016160832 A1 | 10/2016 | | |
| WO | 2018002930 A1 | 1/2018 | | |
| WO | 2018042415 A1 | 3/2018 | | |
| WO | 2018042423 A1 | 3/2018 | | |
| WO | 2018178973 A1 | 10/2018 | | |

OTHER PUBLICATIONS

Quintana et al., (2008) Systems biology approaches for the study of multiple sclerosis. J Cell Mol Med 12(4): 1087-1093.
Ramot et al., (2012) Comparative long-term preclinical safety evaluation of two glatiramoid compounds (Glatiramer Acetate, Copaxone(R), and TV-5010, protiramer) in rats and monkeys. Toxicol Pathol 40(1): 40-54.
Randall et al., Chapter 5: Approaches the the Analysis of Peptides. Peptide and Protein Drug Delivery, edited by Lee VHL. Marcel Dekker, Inc. New York, USA, 1991. pp. 203-246.
Rebif® Product Label (Jun. 2005), Serono, Inc., 20 pages.
Rebif® U.S. Product Label (2003), Serono, Inc., 19 pages.
Reinke Thomas; MS Drug Going Generic Without Making Waves, Managed Care (Jun. 2015), http://bit.ly/1KcyXdE, 17 pages.
Rich et al., (2004) Stepped-care approach to treating MS: a managed care treatment algorithm. J Manag Care Pharm 10(3 Suppl B): S26-S32.
Rothwell et al., (1997) Doctors and patients don't agree: cross sectional study of patients' and doctors' perceptions and assessments of disability in multiple sclerosis. BMJ 314(7094): 1580-1583.
Rovaris et al., (2008) Cognitive impairment and structural brain damage in benign multiple sclerosis. Neurology 71(19): 1521-1526.
Rubinchik et al., (1998) Responsiveness of human skin mast cells to repeated activation: an in vitro study. Allergy 53(1): 14-19.
Rumrill (2009) Multiple Sclerosis: Medical and Psychosocial Aspects, Etiology, Incidence, and Prevalence. Journal of Vocational Rehabilitation 31(2): 75-82.
Ryan and Majno (1977) Acute inflammation. A review. Am J Pathol 86(1): 183-276.
Sage Journals, Table of Contents, http://msj.sagepub.com/content/14/1_suppl.toc (Sep. 2008), 1 page.
Schmeisser et al., (2000) Radioiodination of human interferon—α2 interferes with binding of C-terminal specific antibodies. J Immunol Methods 238(1-2): 81-85.
Schrempf and Ziemssen (2007) Glatiramer acetate: mechanisms of action in multiple sclerosis. Autoimmun Rev 6(7): 469-475.
Selection of Injection Volume. In: Pharmaceutical Preformulation and Formulation; A Practical Guide from Candidate Drug Selection to Commercial Dosage Form. 2nd edition, 2009. Edited by Gibson M. informa healthcare, p. 326.
Shalit et al., (1996) Abstract 650, Copolymer-1 (Copaxone®) Induces a Non-Immunologic Activation of Connective Tissue Type Mast Cells, 97 J. Allergy & Clinical Immunology 97(1): part 3 (Peroutka Dep. Ex. 12), 1 page.

(56) References Cited

OTHER PUBLICATIONS

Shaw Gina; Exorbitant Drug Costs May Price Out Patients. The Washington Diplomat (Uploaded: Apr. 27, 2011). Retrieved on Jan. 26, 2016. 3 pages.
Shire et al., (2004) Challenges in the development of high protein concentration formulations. J Pharm Sci 93(6): 1390-1402. Abstract, 2 pages.
Simpson et al., (2002) Glatiramer Acetate—A Review of its use in Relapsing-Remitting Multiple Sclerosis. Adis Drug Evaluation; CNS Drugs 16(12): 825-850.
Simpson et al., (2002) Glatiramer acetate: a review of its use in relapsing-remitting multiple sclerosis. CNS Drugs 16(12): 825-850.
Singer et al., (2012) Comparative injection-site pain and tolerability of subcutaneous serum-free formulation of InterferonB-1a versus subcutaneous interferonβ-1b: results of the randomized, multicenter, Phase IIIb REFORMS study. BMC Neurol 12: 154, 11 pages.
Soares et al., (2006) Localized panniculitis secondary to subcutaneous glatiramer acetate injections for the treatment of multiple sclerosis: a clinicopathologic and immunohistochemical study. J Am Acad Dermatol 55(6): 968-974.
Sodoyez et al., (1980) 125I-insulin: kinetics of interaction with its receptors and rate of degradation in vivo. Am J Physiol 239(1): E3-E8.
Sorensen et al., (2003) Clinical importance of neutralising antibodies against interferon beta in patients with relapsing-remitting multiple sclerosis. Lancet 362(9391): 1184-1191.
Staton Tracy; Sanofi tags newly OK'd MS drug Lemtrada at $158K, ready to tout head-to-head Rebif data, Fierce Pharma Marketing (Nov. 17, 2014), retrieved on May 27, 2015. http://bit.ly/1QDkTIZ.
Stedman's Medical Dictionary for Health Professions and Nursing; Illustrated 6th edition (2008). Wolter Kluwer; Lippincott Williams & Wilkins. p. 1337.
Stewart and Tran (2012) Injectable multiple sclerosis medications: a patient survey of factors associated with injection-site reactions. Int J MS Care 14(1): 46-53.
Stuart (2004) Clinical management of multiple sclerosis: the treatment paradigm and issues of patient management. J Manag Care Pharm 10(3 Suppl B): S19-S25.
Sumowski et al., (2013) Brain reserve and cognitive reserve in multiple sclerosis: what you've got and how you use it. Neurology 80(24): 2186-2193.
Sustained-release Injectable Products, compiled by J. Senior, Chemistry Industry Press, First version in Sep. 2005, p. 88. with translation of relevant portions, 2 pages.
Table: Approval Timeline, Multiple Sclerosis Drugs. Drugs @ FDA, 2015, 1 page.
Teva News Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis (Jul. 1, 2013). Retrieved on May 22, 2015. 6 pages.
Teva News Release; New Study Demonstrated Significant Reduction in Annualized Relapse Rate and Halting of Disability Progression in MS Patients Switching to Copaxone® (Apr. 14, 2011). 5 pages.
Teva Press Release, Teva Reports First Quarter 2015 Results (Apr. 30, 2015), 14 pages.
Teva Provides Update on Forte Trial (Jul. 7, 2008) Teva Pharmaceutical industries LTD. 2 pages.
Teva Provides Update on Forte Trial Jerusalem, Israel (Jul. 7, 2008) Teva Pharmaceutical industries LTD. 2 pages.
Teva's Shared Solutions® How to Prepare for Your Injection, http://www.copaxone.com/injection-assistance/preparing-your-injection.html (last visited Mar. 7, 2016), 5 pages.
The National MS Society (USA) 2010. Available from: http://www.nationalmssociety.org/about-multiple-sclerosis/what-we-know-about-ms/treatments/index.aspx. Retrieved from: https://web.archive.org/web/20100204190658/http://www.nationalmssociety.org/about-multiple-sclerosis/what-we-know-about-ms/treatments/index.aspx, 4 pages.
Thrower (2007) Clinically isolated syndromes: predicting and delaying multiple sclerosis. Neurology 68(24 Suppl 4): S12-S15. Abstract, 7 pages.
Tintoré et al., (2006) Baseline MRI predicts future attacks and disability in clinically isolated syndromes. Neurology 67(6): 968-972.
Toutain and Bousquet-Mélou (2004) Plasma terminal half-life. J Vet Pharmacol Ther 27(6): 427-439.
Tremlett et al., (2008) Relapses in multiple sclerosis are age- and time-dependent. J Neurol Neurosurg Psychiatry 79(12): 1368-1374.
Tselis et al., (2007) Glatiramer acetate in the treatment of multiple sclerosis. Neuropsychiatr Dis Treat 3(2): 259-267.
Fisniku et al., (2008) Gray matter atrophy is related to long-term disability in multiple sclerosis. Ann Neurol 64(3): 247-254.
Flechter et al., (2002) Comparison of glatiramer acetate (Copaxone) and interferon β-1b (Betaferon) in multiple sclerosis patients: an open-label 2-year follow-up. J Neurol Sci 197(1-2): 51-55.
Flechter et al., (2002) Copolymer 1 (glatiramer acetate) in relapsing forms of multiple sclerosis: open multicenter study of alternate-day administration. Clin Neuropharmacol 25(1): 11-15.
Ford et al., (2006) A prospective open-label study of glatiramer acetate: over a decade of continuous use in multiple sclerosis patients. Mult Scler 12(3): 309-320.
Franklin M and Franz DN; Drug Absorption, Action, and Disposition. In Remington: The Science and Practice of Pharmacy. Paul Beringer ed., 21st edition (2005). Lippincott Williams & Wilkins. pp. 1142-1170, 1167.
Frenken et al., (1994) Analysis of the efficacy of measures to reduce pain after subcutaneous administration of epoetin alfa. Nephrol Dial Transplant 9(9): 1295-1298.
Frick and Pfenniger; Serono to sell Amgen multiple sclerosis drug [Novantrone] in U.S., Firstword Pharma (Nov. 13, 2002), retrieved from <http://bit.ly/1QXqhpR> on May 27, 2015.
Fridkis-Hareli et al., (1999) Binding motifs of copolymer 1 to multiple sclerosis-and rheumatoid arthritis-associated HLA-DR molecules. J Immunol 162(8): 4697-4704.
Friese et al., (2006) The value of animal models for drug development in multiple sclerosis. Brain 129(Pt 8): 1940-1952.
Frohman et al., (2006) Multiple sclerosis—the plaque and its pathogenesis. N Engl J Med 354(9): 942-955.
Gagnon Louise; Every-Other-Day Dosing of Glatiramer Acetate Reduces Adverse Reactions with Comparable Efficacy to Daily Dosing: Presented at WCTRMS, Peerview Press, Sep. 21, 2008, http://www.peerviewpress.com/every-other-day-dosing-glatiramer-acetate-reduces-adverse-reactions-comparable-efficacy-daily-dosing-presented-wctrms (last visited Mar. 8, 2016), 1 page.
Ge et al., (2000) Glatiramer acetate (Copaxone) treatment in relapsing-remitting MS: quantitative MR assessment. Neurology 54(4): 813-817.
Ghose et al., (2007) Transcutaneous immunization with Clostridium difficile toxoid A induces systemic and mucosal immune responses and toxin A-neutralizing antibodies in mice. Infect Immun 75(6): 2826-2832.
Giancarlo Comi, Forte: Results from a phase II, 1-year, Randomized, Double-blind, Parallel-Group, Dose-Comparison Study with Glatiramer Acetate in Relapsing-Remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (Actrims, Ectrims, Lactrims) (2008) 9 pages.
Giovannoni et al., (2015) Is it time to target no evident disease activity (NEDA) in multiple sclerosis? Mult Scler Relat Disord 4(4): 329-333.
Giuliani et al., (2005) Additive effect of the combination of glatiramer acetate and minocycline in a model of MS. J Neuroimmunol 158(1-2): 213-221.

(56) References Cited

OTHER PUBLICATIONS

Gladwell Malcolm; High Prices: How to think about prescription drugs, New Yorker (Oct. 25, 2004), retrieved on Sep. 8, 2012. http://www.newyorker.com/magazine/2004/10/25/high-prices (accessed Feb. 28, 2016), 9 pages.

Glenn et al., (1998) Transcutaneous immunization with cholera toxin protects mice against lethal mucosal toxin challenge. J Immunol 161(7): 3211-3214.

Glenn et al., (2003) Transcutaneous immunization and immunostimulant strategies: capitalizing on the immunocompetence of the skin. Expert Rev Vaccines 2(2): 253-267.

Guideline of Clinical investigation of medicinal products for the treatment of multiple sclerosis EMEA, London Nov. 16, 2006 CPMP/EWP/561/98 Rev .1, pp. 1-12.

Haines et al., (1998) Linkage of the MHC to familial multiple sclerosis suggests genetic heterogeneity. The Multiple Sclerosis Genetics Group. Hum Mol Genet 7(8): 1229-1234.

Helfand Carly; The top 10 best-selling multiple sclerosis drugs of 2013, Fierce Pharma (Sep. 9, 2014), retrieved on May 27, 2015 from <http://bit.ly/1UKrIDd>, 4 pages.

Helfand Carly; Why is Novartis' Copaxone copy lagging? It's all about coverage, analyst explains. Fierce Pharma (Sep. 11, 2015), http://bit.ly/1ia8BNM, 3 pages.

Herper Matthew; Inside The Secret World of Drug Company Rebates. Forbes Pharma & Healthcare (May 10, 2012), http://www.forbes.com/sites/matthewherper/2012/05/10/why-astrazeneca-gives-insurers-60-discounts-on-nexiums-list-price/#155191dd4fd6, 4 pages.

Hestvik et al., (2008) Multiple sclerosis: glatiramer acetate induces anti-inflammatory T cells in the cerebrospinal fluid. Mult Scler 14(6): 749-758.

Hickey (1991) Migration of hematogenous cells through the blood-brain barrier and the initiation of CNS inflammation. Brain Pathol 1(2): 97-105.

Hickey et al., (1991) T-lymphocyte entry into the central nervous system. J Neurosci Res 28(2): 254-260.

Hong et al., (2005) Induction of CD4+CD25+ regulatory T cells by copolymer-I through activation of transcription factor Foxp3. Proc Natl Acad Sci U S A 102(18): 6449-6454.

Hori et al., (2003) Control of regulatory T cell development by the transcription factor Foxp3. Science 299(5609): 1057-1061.

Imming et al., (2006) Drugs, their targets and the nature and number of drug targets. Nat Rev Drug Discov 5(10): 821-834 with Corrigenda.

Yong W. v., et al., Immunological Responses to Different Doses of Glatiramer Acetate in MS: Analyses from the FORTE Trial, poster session dated Apr. 28, 2009, presented at the 61st Annual American Academy of Neurology meeting in Seattle, Washington U.S.A., 1 page.

IMS Health; U.S. Pharmaceutical Market: Trends Issues & Outlook (Sep. 15, 2013), 74 pages.

IMS Institute for Health Informatics; Declining Medicine Use and Costs: for Better or Worse?, Chart Notes (May 2013). 56 pages.

IMS Institute for Health Informatics; Medicine Use and Shifting Costs of Healthcare, Chart Notes (Apr. 2014). 59 pages.

In re Copaxone 40 mg Consolidated Cases, No. 14-01171-GMS, Excerpts from Trial Transcript, D.I. Nos. 282-84, 289-92 (4 pages).

In re Copaxone 40 mg Consolidated Cases, No. 14-01171-GMS, Stipulation and [Proposed] Order Concerning Claim Construction Dispute, D.I. 194 (Feb. 12, 2016), 7 pages.

In re Copaxone 40 mg, No. 1:14-cv-01171-CFC (D. Del.), Trial Tr., ECF No. 282-284, 289-292 (discussing Teva's failed GA Depot) (publicly available). 243 pages.

INFORMS (clinical trials: NCT00731692) from the NIH clinical trials website: clinicaltrials.gov/ct2/show/NCT00731692, retrieved on Nov. 21, 2020. 13 pages.

Introduction to Pharmacokinetics and Pharmacodynamics. In: Concepts in Clinical Pharmacokinetics. 5th edition. Edited by DiPiro et al., 2006. American Society of Health-System Pharmacists. pp. 1-17.

ISR of PCT/IL2010/000679 mailed Dec. 27, 2010, 8pages.

ISR of PCT/IL2012/050138 mailed Aug. 31, 2012, 8 pages.

Jacobs et al., (2000) Intramuscular interferon beta-1a therapy initiated during a first demyelinating event in multiple sclerosis. CHAMPS Study Group. N Engl J Med 343(13): 898-904.

John J. Jessop, Review and Evaluation of Pharmacology Toxicology Data Original NDA Review (1996) (the 1996 FDA SBOA) (attached as Exhibit A to Exh. 1007), 341 pages.

Johnson et al., (1998) Extended use of glatiramer acetate (Copaxone) is well tolerated and maintains its clinical effect on multiple sclerosis relapse rate and degree of disability. Copolymer 1 Multiple Sclerosis Study Group. Neurology 50(3): 701-708. Abstract , 6 pages.

Kansara et al., (2009) Subcutaneous Delivery of Small Molecule Formulations: An Insight into Biopharmaceutics & Formulation Strategies. Drug Deliv Technol 9(6): 38-43.

Katz et al., (2004) Successful Desensitization to Glatiramer Acetate (Copaxone) in Two Patients with Multiple Sclerosis. abstract No. P156. Annual Meeting of the American College of Allergy, Asthma and Immunology; Nov. 7-12, 2003; New Orleans, 2 pages.

Khan et al., "A phase 3 trial to assess the efficacy and safety of glatiramer acetate injections 40mg administered 3 times a week compared to placebo" Oct. 13, 2012; European Committee for Treatment and Research in Multiple Sclerosis, 1 page.

Khan et al., (2009) Glatiramer acetate 20mg subcutaneous twice-weekly versus daily injections: results of a pilot, prospective, randomised, and rater-blinded clinical and MRI 2-year study in relapsing-remitting multiple sclerosis. Multiple Sclerosis 15: S249-S250. Abstract P819, 2 pages.

Khan et al., Randomized, prospective, rater-blinded, four-year, pilot study to compare the effect of daily versus every-other-day glatiramer acetate 20 mg subcutaneous injections in relapsing-remitting multiple sclerosis, 14 Multiple Sclerosis, S296 (2008) 1 page.

Klauer and Zettl (2008) Compliance, adherence and the treatment of multiple sclerosis. J Neurol 255 Suppl 6: 87-92.

Kleiner et al., (2010) Immunological Response to Glatiramer Acetate in MS Patients after Different Pretreatments—The CopImmunoNet Study. Neurology 74 (Suppl 2): A554, abstract P06.178.

Kragt et al., (2006) How similar are commonly combined criteria for EDSS progression in multiple sclerosis? Mult Scler 12(6): 782-786.

Lambert and Laurent (2008) Intradermal vaccine delivery: will new delivery systems transform vaccine administration? Vaccine 26(26): 3197-3208.

Lando et al., (1979) Effect of cyclophosphamide on suppressor cell activity in mice unresponsive to EAE. J Immunol 123(5): 2156-2160.

LeBano Lauren (2012) Gray Matter Atrophy May Serve as an Effective Outcome measure for MS Clinical Trials. Neurology Reviews 20(2): 8. 5 pages.

Lisak RP and Kira J-I 'Chapter 100, Multiple Sclerosis'. In: International Neurology a Clinical Approach. Edited by: Lisak et al., pp. 366-374, Wiley-Blackwell.

Lobel et al., (1996) Copolymer-1. Drugs of the Future 21(2): 131-134.

Lublin et al., (2003) Effect of relapses on development of residual deficit in multiple sclerosis. Neurology 61(11): 1528-1532.

Luzzio C & Keegan BM Multiple Sclerosis Medication, Medscape Reference (Nov. 24, 2014), retrieved on May 28, 2015. http://emedicine.medscape.com/article/1146199-medication#1, 18 pages.

Manso and Sokol (2006) Life cycle management of ageing pharmaceutical assets. Pharmaceutical Law Insight 3(7): 16-19.

Marketing Materials, PRA, Multiple Sclerosis: Transform Your Clinical Trial with PRA (2012) (on file with author) (Peroutka Dep. Ex. 4) 2 pages.

McBride (2002) Nonadherence to immunomodulation in multiple sclerosis. Int'l J MS Care 4: 85. Presented at the Second International Multiple Sclerosis Week. Multiple Sclerosis: A World View. Hyatt Regency Chicago, Illinois, USA; Jun. 5-9, 2002, 2 pages.

McDonald et al., (2001) Recommended diagnostic criteria for multiple sclerosis: Guidelines from the international panel on the diagnosis of multiple sclerosis. Annals of Neurology 50(1): 121-127.

(56) References Cited

OTHER PUBLICATIONS

McEwan et al., (2010) Best Practices in Skin Care for the Multiple Sclerosis Patient Receiving Injectable Therapies. Int J MS Care 12(4): 177-189.
McKeage (2015) Glatiramer Acetate 40 mg/ml in Relapsing-Remitting Multiple Sclerosis: A Review. CNS Drugs; Published online: Apr. 24, 2015. 8 pages.
Medical News Today; Multiple Sclerosis—Teva Provides Update on FORTE Trial. Article Date: Jul. 8, 2008. Retrieved from: https://web.archive.org/web/20090103103610/http://www.medicalnewstoday.com/articles/114183.php; 3 pages.
Meibohm and Derendorf (1997) Basic concepts of pharmacokinetic/pharmacodynamic (PK/PD) modelling. Int J Clin Pharmacol Ther 35(10): 401-413.
Meiner Z et al., (1997) Copolymer 1 in relapsing-remitting multiple sclerosis: a multi-centre trial. In: Frontiers in Multiple Sclerosis: Clinical Research and Therapy. Edited by Abramsky O and Ovadia Hpp. 213-221.
Mendes and Sá (2011) Classical immunomodulatory therapy in multiple sclerosis: how it acts, how it works. Arq Neuropsiquiatr 69(3): 536-543.
Menge et al., (2008) Disease-modifying agents for multiple sclerosis: recent advances and future prospects. Drugs 68(17): 2445-2468.
Miller (2004) The importance of early diagnosis of multiple sclerosis. J Manag Care Pharm 10(3 Suppl B): S4-S11.
Miller et al., (1998) Treatment of multiple sclerosis with copolymer-1 (Copaxone®): implicating mechanisms of Th1 to Th2/Th3 immune-deviation. J Neuroimmunol 92(1-2): 113-121.
Miller et al., (2005) Clinically isolated syndromes suggestive of multiple sclerosis, part I: natural history, pathogenesis, diagnosis, and prognosis. Lancet Neurol 4(5): 281-288. Abstract, 2 pages.
Miller et al., (2005) Clinically isolated syndromes suggestive of multiple sclerosis, part 2: non-conventional MRI, recovery processes, and management. Lancet Neurol 4(6): 341-348. Abstract, 2 pages.
Miller et al., (2007) Experimental autoimmune encephalomyelitis in the mouse. Current Protocols in Immunology 15.1.1-15.1.13.
Milo and Miller (2014) Revised diagnostic criteria of multiple sclerosis. Autoimmun Rev 13(4-5): 518-524.
Minneboo et al., (2008) Predicting short-term disability progression in early multiple sclerosis: added value of MRI parameters. J Neurol Neurosurg Psychiatry 79(8): 917-923.
MomentumMagazineOnline.com; 10 Disease-Modifying Treatments, Nov. 2013, available at http://bit.ly/1eVa0jT, 1 page.
Monro (1993) The paradoxical lack of interspecies correlation between plasma concentrations and chemical carcinogenicity. Regul Toxicol Pharmacol 18(1): 115-135.
Neuhaus et al., (2000) Multiple sclerosis: comparison of copolymer-1-reactive T cell lines from treated and untreated subjects reveals cytokine shift from T helper 1 to T helper 2 cells. Proc Natl Acad Sci U S A 97(13): 7452-7457.
Neuhaus et al., (2001) Mechanisms of action of glatiramer acetate in multiple sclerosis. Neurology 56(6): 702-708.
Neuhaus et al., (2003) Immunomodulation in multiple sclerosis: from immunosuppression to neuroprotection. Trends Pharmacol Sci 24(3): 131-138. Abstract, 2 pages.
Neuhaus et al., (2007) Pharmacokinetics and pharmacodynamics of the interferon-betas, glatiramer acetate, and mitoxantrone in multiple sclerosis. J Neurol Sci 259(1-2): 27-37.
Noseworthy et al., (2000) Multiple sclerosis. N Engl J Med 343(13): 938-952.
O'Connor et al., (2009) 250 microg or 500 microg interferon beta-1b versus 20 mg glatiramer acetate in relapsing-remitting multiple sclerosis: a prospective, randomised, multicentre study. Lancet Neurol 8(10): 889-897 with errata.
Oksenberg et al., (1992) A single amino-acid difference confers major pharmacological variation between human and rodent 5-HT1B receptors. Nature 360(6400): 161-163.
O'Neill (1997) Secondary endpoints cannot be validly analyzed if the primary endpoint does not demonstrate clear statistical significance. Controlled Clinical Trials 18(6): 550-556.
Opinion, Endo Pharmaceuticals, Inc. v. Mylan Pharmaceuticals, Inc., No. 11-cv-00717, Document 226 (D. Del. Jan. 28, 2014) (Peroutka Dep. Ex. 6). 108 pages.
Orange Book: Approved Drug Products with Therapeutic Equivalence Evaluations. Retrieved from: http://www.accessdata.fda.gov/scripts/cder/ob/docs/patexclnew.cfm?Appl_No=020622&Product_No=003&table1=OB_Rx (accessed Feb. 5, 2015). 7 pages.
Orelli Brian; Momenta Slowed (Temporarily), The Motley Fool (Nov. 7, 2015), retrieved on Dec. 28, 2015. http://bit.ly/1YiNNmS.
O'Riordan et al., (1998) The prognostic value of brain MRI in clinically isolated syndromes of the CNS. A 10-year follow-up. Brain 121 (Pt 3): 495-503.
Osborne (2009) Buzz around Campath proof-of-concept trial in MS. Nat Biotechnol 27(1): 6-8.
Paolillo et al., (2004) The relationship between inflammation and atrophy in clinically isolated syndromes suggestive of multiple sclerosis: a monthly MRI study after triple-dose gadolinium-DTPA. J Neurol 251(4): 432-439.
Pardo et al., (2007) Impact of an oral antihistamine on local injection site reactions with glatiramer acetate. Multiple Sclerosis 13: S134. Abstract P455.
Partidos et al., (2003) Immunity under the skin: potential application for topical delivery of vaccines. Vaccine 21(7-8): 776-780.
Paty (1994) The interferon-β1b clinical trial and its implications for other trials. Ann Neurol 36 Suppl: S113-S114.
Pelidou et al., (2008) Multiple sclerosis presented as clinically isolated syndrome: the need for early diagnosis and treatment. Ther Clin Risk Manag 4(3): 627-630.
Peroutka (1988) Antimigraine drug interactions with serotonin receptor subtypes in human brain. Ann Neurol 23(5): 500-504.
Pert and Snyder (1973) Properties of opiate-receptor binding in rat brain. Proc Natl Acad Sci U S A 70(8): 2243-2247.
Petty et al., (1994) The effect of systemically administered recombinant human nerve growth factor in healthy human subjects. Ann Neurol 36(2): 244-246.
"Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL: www.tevapharm.com/Media/News/Pages/2012/1743500.aspx?year-2012&page> 3 pages.
"Design and development of sustained release or controlled release agents", chief edited by Yaodong Yan, Chinese medical science and technology press, First edition on May 2006; pp. 10-29. Translation of relevant portions.
1996 FDA Meeting Agenda minutes from the Peripheral and Central Nervous System Drug Advisory Committee (dated Sep. 19, 1996) (Exhibit A to Exhibit 1019).
3-Times-A-Week Copaxone® 40 MG, TEVA. Retrieved from: https://www.copaxone.com/about-copaxone/copaxone-40-mg on Mar. 10, 2016.
A Multinational, Multicenter, Randomized, Double-Blind, Placebo-Controlled, Parallel-Group Study to Assess the Efficacy, Tolerability and Safety of 40 mg Glatiramer Acetate Injection in Subjects with Amyotrophic Lateral Sclerosis. Protocol ALS-GA-201 (GoALS); Eudract No. 2006-001688-49. Summary of Clinical Trial Results; Jul. 2008. Publication date: Feb. 9, 2018 Retrieved from: https://www.clinicaltrialsregister.eu/ctr-search/trial/2006-001688-49/GB; 62 pages.
A Pilot, Multi-Center, Open-Label, One-Group Study to Explore the Efficacy, Tolerability and Safety of an Oral Once-daily 600 mg Dose of Glatiramer Acetate (GA) in Subjects with Relapsing Remitting (R-R) Multiple Sclerosis (MS). Protocol GA/7026; EudraCT No. 2004-000463-94. Study Conducted (Sep. 2004-Mar. 2006). Summary of Results; Feb. 2007. Publication date: Jan. 4, 2017. Retrieved from: https://www.clinicaltrialsregister.eu/ctr-search/trial/2004-000463-94/results; 24 pages.
A Study to Test the Effectiveness and Safety of a New Higher 40mg Dose of Copaxone® Compared to Copaxone® 20mg, the Currently

(56) References Cited

OTHER PUBLICATIONS

Approved Dose [online]. ClinicalTrials.gov, 1993 [retrieved on Feb. 13, 2015]. Retrieved from the Internet: <URL: clinicaltrials.gov/show/NCT00202982>; 6 pages.
A to Z of MS Alemtuzumab (Lemtrada), Multiple Sclerosis Trust, retrieved on Jun. 2, 2015. http://bit.ly/1YnIfHQ.
Abramsky et al., (1977) Effect of a synthetic polypeptide (COP 1) on patients with multiple sclerosis and with acute disseminated encephalomeylitis. Preliminary report. J Neurol Sci 31(3): 433-438.
Aharoni (2013) The mechanism of action of glatiramer acetate in multiple sclerosis and beyond. Autoimmun Rev 12(5): 543-553.
Aharoni et al., (1997) Copolymer 1 induces T cells of the T helper type 2 that crossreact with myelin basic protein and suppress experimental autoimmune encephalomyelitis. Proc Natl Acad Sci U S A 94(20): 10821-10826.
Aharoni et al., (2000) Specific Th2 cells accumulate in the central nervous system of mice protected against experimental autoimmune encephalomyelitis by copolymer 1. Proc Natl Acad Sci U S A 97(21): 11472-11477.
Aharoni et al., (2003) Glatiramer acetate-specific T cells in the brain express T helper 2/3 cytokines and brain-derived neurotrophic factor in situ. Proc Natl Acad Sci U S A 100(24): 14157-14162.
Aharoni et al., (2005) Therapeutic effect of the immunomodulator glatiramer acetate on trinitrobenzene sulfonic acid-induced experimental colitis. Inflamm Bowel Dis 11(2): 106-115.
Alison Palkhivala; Doubling the Dose of Glatiramer Acetate Does Not Increase Efficacy. Medscape Medical News (Sep. 22, 2008). Retrieved on Jan. 6, 2015. 2 pages.
All About MS. Posted by: Thixia | Apr. 11, 2008. Rtrieved from: https://scamparoo.wordpress.com/2008/04/11/ms-therapies-copaxone/ (dated Apr. 11, 2008 (accessed Feb. 5, 2015)), 11 pages.
Ampyra Prescribing Information, Acorda Therapeutics (Dec. 2014), 9 pages.
Anand Geeta; Through Charities, Drug Makers Help People—and Themselves, Wall St. J. (Dec. 1, 2005), retrieved on Mar. 8, 2016 http://www.wsj.com/articles/SB113339802749110822, 10 pages.
Anderson and Shive (1997) Biodegradation and biocompatibility of PLA and PLGA microspheres. Advanced Drug Delivery Reviews 28: 5-24.
Anderson et al., (1992) Revised estimate of the prevalence of multiple sclerosis in the United States. Ann Neurol 31(3): 333-336.
Anderson et al., (2010) Injection pain decreases with new 0.5 mL formulation of glatiramer acetate. International Journal of MS Care 12(supp 1): 54. Abstracts from the 24th Annual Meeting of the Consortium of Multiple Sclerosis Centers; Multiple Sclerosis: Sustaining Care, Seeking a Cure, Jun. 2-5, 2010; San Antonio, TX, USA.
Anderson et al., (2010) Tolerability and safety of novel half milliliter formulation of glatiramer acetate for subcutaneous injection: an open-label, multicenter, randomized comparative study. J Neurol 257(11): 1917-1923.
Arnon (1996) The development of Cop 1 (Copaxone®), an innovative drug for the treatment of multiple sclerosis: personal reflections. Immunol Lett 50(1-2): 1-15.
Arnon and Aharoni (2004) Mechanism of action of glatiramer acetate in multiple sclerosis and its potential for the development of new applications. Proc Natl Acad Sci U S A 101 Suppl 2(Suppl 2): 14593-14598.
Arnon and Aharoni (2007) Neurogenesis and neuroprotection in the CNS-fundamental elements in the effect of Glatiramer acetate on treatment of autoimmune neurological disorders. Mol Neurobiol 36(3): 245-253.
Avonex® (Interferon beta-1a), Product Label (2006) 39 pages.
Bains et al., (2010) Glatiramer acetate: successful desensitization for treatment of multiple sclerosis. Ann Allergy Asthma Immunol 104(4): 321-325.
Bakshi et al., (2005) Imaging of multiple sclerosis: role in neurotherapeutics. NeuroRx 2(2): 277-303.
Bari (2010) A prolonged release parenteral drug delivery system—an overview. Int J Pharm Rev and Res 3(1): 1-11.
Bartus et al., (1998) Sustained delivery of proteins for novel therapeutic products. Science 281(5380): 1161-1162.
Beer et al., (2011) The prevalence of injection-site reactions with disease-modifying therapies and their effect on adherence in patients with multiple sclerosis: an observational study. BMC Neurol 11: 144.
Benet LZ et al., Pharmacokinetics: The Dynamics of Drug Absorption, Distribution, and Elimination. In: Goodman & Gilman's The Pharmacological Basis of Therapeutics, 9th edition. McGraw-Hill, 1996. pp. 3-27.
Beringer P and Winter ME; Clinical Pharmacokinetics and Pharmacodynamics. In Remington: The Science and Practice of Pharmacy. Paul Beringer ed., 21st edition (2005). Lippincott Williams & Wilkins. pp. 1191-1205, 1197, 1201.
Bermel and Bakshi (2006) The measurement and clinical relevance of brain atrophy in multiple sclerosis. Lancet Neurol 5(2): 158-170.
Berndt et al., (1995) Information, marketing, and pricing in the U.S. antiulcer drug market. Am Econ Rev 85(2): 100-105.
Berndt et al., (2002) An analysis of the diffusion of new antidepressants: variety, quality, and marketing efforts. J Ment Health Policy Econ 5(1): 3-19.
Betaseron® U.S. Product Label (Oct. 2003), 2 pages.
Bjartmar and Fox (2002) Pathological mechanisms and disease progression of multiple sclerosis: therapeutic Implications. Drugs Today (Barc) 38(1): 17-29.
Blanco et al., (2006) Effect of glatiramer acetate (Copaxone®) on the immunophenotypic and cytokine profile and BDNF production in multiple sclerosis: a longitudinal study. Neurosci Lett 406(3): 270-275.
Boissel and Nony (2002) Using pharmacokinetic-pharmacodynamic relationships to predict the effect of poor compliance. Clin Pharmacokinet 41(1): 1-6.
Bornstein, M.B., Johnson, K.P. (1992). Treatment of Multiple Sclerosis with Copolymer I. In: Rudick, R.A., Goodkin, D.E. (eds) Treatment of Multiple Sclerosis. Clinical Medicine and the Nervous System. Springer, London. https://doi.org/10.1007/978-1-4471-3184-7_8, Abstract only, 1 page.
Bornstein et al., "Clinical Trials of a Synthetic Polypeptide (Copolymer 1) for the treatment of Mutliple Sclerosis". In: Gonsett et al., Immunological and Clinical Aspects of Multiple Sclerosis (MTP Press, The Hague, 1984), pp. 144-150. Abstract, 1 page.
Bornstein et al., (1980) Treatment of multiple sclerosis with a synthetic polypeptide: preliminary results. Trans Am Neurol Assoc 105: 348-350.
Bornstein et al., (1982) Multiple sclerosis: trial of a synthetic polypeptide. Ann Neurol 11(3): 317-319.
Bornstein et al., (1984) Clinical trials of copolymer I in multiple sclerosis. Ann N Y Acad Sci 436: 366-372.
Bornstein et al., (1987) A pilot trial of Cop 1 in exacerbating-remitting multiple sclerosis. N Engl J Med 317(7): 408-414.
Bornstein et al., (1988) Clinical experience with COP-1 in multiple sclerosis. Neurology 38(7 Suppl 2): 66-69. Abstract 1 page.
Bornstein et al., (1991) A placebo-controlled, double-blind, randomized, two-center, pilot trial of Cop 1 in chronic progressive multiple sclerosis. Neurology 41(4): 533-539.
Bornstein; Clinical Experience: hopeful prospects in multiple sclerosis:. Hospital Practice (Off. Ed.), 1992, vol. 27, No. 5, pp. L135-158, 141-142, 145-158. 1st page.
Brunkow et al., (2001) Disruption of a new forkhead/winged-helix protein, scurfin, results in the fatal lymphoproliferative disorder of the scurfy mouse. Nat Genet 27(1): 68-73.
Abramsky et al., (1982) Alpha-fetoprotein suppresses experimental allergic encephalomyelitis. J Neuroimmunol 2(1): 1-7.
Aharoni et al., (1998) Bystander suppression of experimental autoimmune encephalomyelitis by T cell lines and clones of the Th2 type induced by copolymer 1. J. Neuroimmunol. 91(1-2): 135-146.
Aharoni et al., (2005) The immunomodulator glatiramer acetate augments the expression of neurotrophic factors in brains of experimental autoimmune encephalomyelitis mice. Proc Natl Acad Sci USA 102(52): 19045-19050.

(56) References Cited

OTHER PUBLICATIONS

Aharoni et al., (2008) Demyelination arrest and remyelination induced by glatiramer acetate treatment of experimental autoimmune encephalomyelitis. Proc Natl Acad Sci USA 105(32): 11358-11363.

Anderson and Shive (1997) Biodegradation and biocompatibility of PLA and PLGA microspheres. Adv Drug Deliv Rev 28(1): 5-24.

Armstrong et al., (1997) A novel synthesis of disubstituted ureas using titanium (IV) isopropoxide and sodium borohydride. Tetrahedron Letters 38(9): 1531-1532.

Artuso et al., (2007) Preparation of mono-, di-, and trisubstituted ureas by carbonylation of aliphatic amines with S,S-dimethyl dithiocarbonate. Synthesis 22: 3497-3506.

Barun and Bar-Or (2011) Treatment of multiple sclerosis with anti-CD20 antibodies. Clin Immunol 142(1): 31-37.

Ben-Nun et al., (1996) The autoimmune reactivity to myelin oligodendrocyte glycoprotein (MOG) in multiple sclerosis is potentially pathogenic: effect of copolymer 1 on MOG-induced disease. J Neurol 243(4 Suppl 1): S14-S22.

Blanchette and Neuhaus (2008) Glatiramer acetate: evidence for a dual mechanism of action. J Neurol 255 Suppl 1: 26-36.

Bleich Kimelman et al., "Glatiramer Acetate Depot: Towards Clinical Application". International Joint Israel-Greek-Italian Neuroimmunological Meeting (ISNI), Elounda, Crete, Greece Jun. 11-14, 2015. Presentation; 25 pages.

Bleich Kimelman et al., "Pre-clinical studies and evaluation of treatment need of glatiramer acetate depot". Presented at the 31st Congress of the European Committee for Treatment and Research in Multiple Sclerosis (ECTRIMS) 2015: Oct. 7-15, Barcelona, Spain. Retrieved from: http://www.mapi-pharma.com/wp-content/uploads/2015/10/ECTRIMS-Barcelona-Oct.-8-2015-Mapi-Pharma-Poster.pdf. Poster; 1 page.

Bleich-Kimelman et al., (2016) Pre-Clinical Studies and Evaluation of Treatment Need of Glatiramer Acetate Depot (Long Acting Injection) (P5.314). Neurology 86 (16 Supplement). 2 pages.

Bleich Kimelman et al., "Pre-Clinical Studies and Evaluation of Treatment Need of Glatiramer Acetate Depot (Long Acting Injection of GA)". The 68th Meeting of the Annual American Academy of Neurology (AAN), Apr. 15-21, 2016, Vancouver, Canada. Poster; 1 page.

Bleich-Kimelman et al., (2015) Pre-clinical studies and evaluation of treatment need of glatiramer acetate depot. Multiple Sclerosis Journal 21(S11): 688; EP1320.

Bleich-Kimelman et al., (2015) Pre-clinical studies and evaluation of treatment need of glatiramer acetate depot. Abstract release date: Sep. 23, 2015. Retrieved from: https://onlinelibrary.ectrims-congress.eu/ectrims/2015/31st/115168/hadav.bleich-kimelman.pre-clinical.studies.and.evaluation.of.treatment.need.of.html on May 16, 2022 (paper copy total 2 pages). Published in final edited version in Multiple Sclerosis Journal 21(S11): 688, EP 1320.

Bodmer et al., (1992) Factors influencing the release of peptides and proteins from biodegradable parenteral depot systems. Journal of Controlled Release 21(1-3): 129-137.

Bolton et al., (1982) Immunosuppression by cyclosporin A of experimental allergic encephalomyelitis. J Neurol Sci 56(2-3): 147-153.

Bomprezzi et al., (2011) Glatiramer acetate-specific antibody titres in patients with relapsing/remitting multiple sclerosis and in experimental autoimmune encephalomyelitis. Scand J Immunol 74(3): 219-226 with Corrigendum.

Bornstein et al. 1990, Clinical trials of Cop 1 in multiple sclerosis, in Handbook of Multiple Sclerosis, ed. Cook S.D. Marcel Dekker, Inc., pp. 469-480.

Brenner et al., (2001) Humoral and cellular immune responses to Copolymer 1 in multiple sclerosis patients treated with Copaxone. J Neuroimmunol 115(1-2): 152-160.

Bright et al., (1999) Tyrphostin B42 inhibits IL-12-induced tyrosine phosphorylation and activation of Janus kinase-2 and prevents experimental allergic encephalomyelitis. J Immunol 162(10): 6255-6262.

Brown (2005) Commercial challenges of protein drug delivery, Expert Opinion on Drug Delivery. Informa Healthcare, GB 2(1): 29-42.

Bouissou et al., (2006) The Influence of Surfactant on PLGA Microsphere Glass Transition and Water Sorption: Remodeling the Surface Morphology to Attenuate the Burst Release. Pharmaceutical Research 23(6): 1295-1305.

Cohen et al., (2007) Randomized, double-blind, dose-comparison study of glatiramer acetate in relapsing-remitting MS. Neurology 68(12): 939-944.

Comi et al., (2011) Phase III dose-comparison study of glatiramer acetate for multiple sclerosis. Ann Neurol 69(1): 75-82.

Constantinescu et al., (2011) Experimental autoimmune encephalomyelitis (EAE) as a model for multiple sclerosis (MS). Br J Pharmacol 164(4): 1079-1106.

Correale et al., (2017) Progressive multiple sclerosis: from pathogenic mechanisms to treatment. Brain 140(3): 527-546.

Doshi and Chataway (2016) Multiple sclerosis, a treatable disease. Clin Med (Lond) 16(Suppl 6): s53-s59.

Fridkis-Hareli (2013) Design of Peptide Immunotherapies for MHC Class-II-Associated Autoimmune Disorders. Clin Dev Immunol. 2013: 826191; 9 pages.

Fridkis-Hareli et al., (1999) Binding of random copolymers of three amino acids to class II MHC molecules. Int Immunol 11(5): 635-641.

Goodson JM: Dental applications; in Langer LS, Wise DL (eds): Medical Applications of Controlled Release. Boca Raton, CRC Press, 1984, vol. 2, pp. 115-138.

Hawker (2011) Progressive multiple sclerosis: characteristics and management. Neurol Clin 29(2): 423-434.

Johnson et al., (1995) Copolymer 1 reduces relapse rate and improves disability in relapsing-remitting multiple sclerosis. Results of a phase III multicenter, double-blind, placebo-controlled trial. Neurology 45(7): 1268-1276.

Karussis et al., (2010) Long-term treatment of multiple sclerosis with glatiramer acetate: natural history of the subtypes of anti-glatiramer acetate antibodies and their correlation with clinical efficacy. J Neuroimmunol 220(1-2): 125-130.

Khan et al., (2013) Three times weekly glatiramer acetate in relapsing-remitting multiple sclerosis. Ann Neurol 73(6): 705-713.

Kleinman et al., (2010) Medication adherence with disease modifying treatments for multiple sclerosis among US employees. J Med Econ 13(4): 633-640.

Kurtzke (1983) Rating neurologic impairment in multiple sclerosis: an expanded disability status scale (EDSS). Neurology 33(11): 1444-1452.

Langer (1990) New Methods of Drug Delivery, Science, US 249(4976): 1527-1533.

Margolis et al., (2011) Disease-modifying drug initiation patterns in commercially insured multiple sclerosis patients: a retrospective cohort study. BMC Neurol 11: 122; 10 pages.

McKay et al., (2015) Risk factors associated with the onset of relapsing-remitting and primary progressive multiple sclerosis: a systematic review. Biomed Res Int 2015: 817238; 11 pages.

Miller et al., "Glatiramer acetate depot (extended-release) phase IIa one-year study in patients with relapsing remitting multiple sclerosis: safety, tolerability and efficacy (NEDA) analysis". 7th Joint ECTRIMS—ACTRIMS Meeting Oct. 25-28, 2017, Paris, France. Abstract; 2 pages.

Miller et al., "Glatiramer acetate depot (extended-release) phase IIa one-year study in patients with relapsing remitting multiple sclerosis: safety, tolerability and efficacy (NEDA) analysis". 7th Joint ECTRIMS—ACTRIMS Meeting Oct. 25-28, 2017, Paris, France. Poster; 1 page.

Miller et al., "Glatiramer Acetate Depot (extended-release) Phase IIA study in patients with Relapsing Remitting Multiple Sclerosis: Six months' interim analysis". 7th Joint ECTRIMS—ACTRIMS Meeting Oct. 25-28, 2017, Paris, France. Poster; 1 page.

Nyska et al., (2014) Histopathology of biodegradable polymers: challenges in interpretation and the use of a novel compact MRI for biocompatibility evaluation. Polym Adv Technol 25(5): 461-467.

(56) References Cited

OTHER PUBLICATIONS

Oleen-Burkey et al., (2011) The relationship between alternative medication possession ratio thresholds and outcomes: evidence from the use of glatiramer acetate. J Med Econ 14(6): 739-747.
Burger et al., (2009) Glatiramer acetate increases IL-1 receptor antagonist but decreases T cell-induced IL-1β in human monocytes and multiple sclerosis. Proc Natl Acad Sci U S A 106(11): 4355-4359.
Caon et al., (2009) Randomized, Prospective, Rater-Blinded, Four Year Pilot Study to Compare the Effect of Daily Versus Every Other Day Glatiramer Acetate 20 mg Subcutaneous Injections in RRMS Neurology 72:11(3): A317, 1 page.
Castells (2009) Rapid desensitization for hypersensitivity reactions to medications. Immunol Allergy Clin North Am 29(3): 585-606.
Chabot et al., (2002) Cytokine production in T lymphocyte-microglia interaction is attenuated by glatiramer acetate: a mechanism for therapeutic efficacy in multiple sclerosis. Mult Scler 8(4): 299-306.
Chantelau et al., (1991) What makes insulin injections painful? BMJ 303(6793): 26-27.
Chapter 8: Drug elimination and pharmacokinetics. pp. 106-119. H.P. Pharmacology (5th ed. 2005); edited by Rang HP, Dale MM, Ritter JM and Moore PK, 22 pages.
Chen et al., (1991) Mu receptor binding of some commonly used opioids and their metabolites. Life Sci 48(22): 2165-2171.
Chen et al., (2002) Sustained immunological effects of Glatiramer acetate in patients with multiple sclerosis treated for over 6 years. J Neurol Sci 201(1-2): 71-77.
Cohen et al., (2012) Alemtuzumab versus interferon beta 1a as first-line treatment for patients with relapsing-remitting multiple sclerosis: a randomised controlled phase 3 trial. Lancet 380(9856): 1819-1828.
Comi and Moiola (2002) Glatiramer acetate. Neurologia 17(5): 244-258.
Comi et al., (2001) European/Canadian multicenter, double-blind, randomized, placebo-controlled study of the effects of glatiramer acetate on magnetic resonance imaging—measured disease activity and burden in patients with relapsing multiple sclerosis. European/Canadian Glatiramer Acetate Study Group. Ann Neurol 49(3): 290-297.
Comi et al., (2008) Results from a phase III, 1-year, Randomized, Double-blind, Parallel-Group, Dose-Comparison Study with Glatiramer Acetate in Relapsing-Remitting Multiple Sclerosis. Mult Scler 14: S299-S301, 3 pages.
Comi et al., (2009) Effect of glatiramer acetate on conversion to clinically definite multiple sclerosis in patients with clinically isolated syndrome (PreCISe study): a randomised, double-blind, placebo-controlled trial. Lancet 374(9700): 1503-1511.
Comi G. "Treatment with glatiramer acetate delays conversion to clinically definite multiple sclerosis (CDMS) in patients with clinically isolated syndromes (CIS)". Program and abstracts of the American Academy of Neurology 60th Annual Meeting; Apr. 12-19, 2008; Chicago, Illinois. LBS.003, 1 page.
Conner (2014) Glatiramer acetate and therapeutic peptide vaccines for multiple sclerosis. Journal of Autoimmunity and Cell Responses 1: Article 3; 11 pages.
Copaxone 20 mg/ml or Copaxone 40 mg/ml, NDA 020622/S-089 FDA Approved Labeling Text dated Jan. 28, 2014, 31 pages.
Copaxone 20 mg/ml, Solution for Injection, Pre-Filled Syringe, Summary of Product Characteristics updated on Apr. 17, 2009, 7 pages.
Copaxone Prescribing Information, TEVA Pharmaceuticals USA, Inc., (Jan. 2014). 8 pages.
Copaxone, retrieved from <https://scamparoo.wordpress.com/2008/04/11/ms-therapies-copaxone> dated Apr. 11, 2008 (accessed Feb. 5, 2015), 11 pages.
Copaxone® U.S. Product Label (2001), TEVA Pharmaceutical Industries, Ltd., 26 pages.
Copaxone® U.S. Product Label (Feb. 2009), TEVA Pharmaceuticals USA, Inc., 22 pages.
Copaxone®, Food and Drug Administration Approved Labeling, Jan. 2014, submitted as Exhibit 1057 in Inter Partes Review Case No. IPR2015-00643, 8 pages.
Copaxone®, Physicians' Desk Reference, 62nd ed. Montvale, NJ, Thomson Healthcare Inc., pp. 3231-3235 (2008).
Costello et al., (2008) Recognizing nonadherence in patients with multiple sclerosis and maintaining treatment adherence in the long term. Medscape J Med 10(9): 225, 14 pages.
David J and Stewart MB; Commercial Success: Economic Principles Applied to Patent Litigation. In: Economic Damages in Intellectual Property: A Hands-On Guide to Litigation. Edited by Slottje D. John Wiley & Sons, Inc. 2006. pp. 159-170.
De Stefano et al., (2009) The results of two multicenter, open-label studies assessing efficacy, tolerability and safety of protiramer, a high molecular weight synthetic copolymeric mixture, in patients with relapsing-remitting multiple sclerosis. Mult Scler 15(2): 238-243.
De Stefano et al., (2010) Assessing brain atrophy rates in a large population of untreated multiple sclerosis subtypes. Neurology 74(23): 1868-1876.
De Vijlder (2003) Primary congenital hypothyroidism: defects in iodine pathways. Eur J Endocrinol 149(4): 247-256.
Devonshire et al., (2006) The Global Adherence Project—A multicentre observational study on adherence to disease-modifying therapies in patients suffering from relapsing-remitting multiple sclerosis, Multiple Sclerosis 12: S1 (P316).
Dhib-Jalbut (2002) Mechanisms of action of interferons and glatiramer acetate in multiple sclerosis. Neurology 58(8 Suppl 4): S3-S9.
Dhib-Jalbut (2003) Glatiramer acetate (Copaxone) therapy for multiple sclerosis. Pharmacol Ther 98(2): 245-255. Abstract, 2 pages.
DiPiro et al., Introduction to pharmacokinetics and pharmacodynamics. In: Concepts in Clinical Pharmacodynamics (5th ed. 2010). pp. 1-17.
Duda et al., (2000) Glatiramer acetate (Copaxone®) induces degenerate, Th2-polarized immune responses in patients with multiple sclerosis. J Clin Invest 105(7): 967-976.
Edgar et al., (2004) Lipoatrophy in patients with multiple sclerosis on glatiramer acetate. Can J Neurol Sci 31(1): 58-63.
Efimova et al., (2005) Changes in the secondary structure of proteins labeled with 125I: CD spectroscopy and enzymatic activity studies. Journal of Radioanalytical and Nuclear Chemistry 264(1): 91-96.
Extavia® Product Label (2009). Prescribing information, 5 pages.
Extavia®, Abbreviated Drug Monograph: Interferon beta 1b (Extavia®), Sep. 2010, submitted as Exhibit 1053 in Inter Partes Review Case Nos. IPR2015-00643, IPR2015-00644 and IPR2015-00830, 5 pages.
Farina et al., (2001) Treatment of multiple sclerosis with Copaxone (COP): Elispot assay detects COP-induced interleukin-4 and interferon-gamma response in blood cells. Brain 124(Pt 4): 705-719.
FDA approves new MS treatment regimen developed at Wayne State University by Dr. Omar Khan, Division of Research—Research@Wayne, https://research.wayne.edu/rwnews/article.php?id=1319 (Posted on: Thursday, Jan. 30, 2014; last visited Mar. 8, 2016).
FDA Guidance for Industry—Population Pharmacokinetics (1999). 35 pages.
FDA Guidance for Industry—Statistical Approaches to Establishing Bioequivalence (2001). 48 pages.
FDA, Guideline for Industry: Dose-Response Information to Support Drug Registration (1994)0 17 pages.
Figure: Perception of 3-times-a-week Copaxone 40mg compared to Daily Copaxone 20mg. 2015.
Figure: Perceptions of Copaxone® 40mg compared to Daily Generic GA. 2015.
Figure: Perceptions of Copaxone® 40mg vs. 20mg. 2015.
Figure: Rationale for Discussing 20mg and 40mg for First Line Patients. 2015.
Figure: Rationale for Requesting Copaxone. 2015.
Filippi et al., (2006) Effects of oral glatiramer acetate on clinical and MRI-monitored disease activity in patients with relapsing multiple sclerosis: a multicentre, double-blind, randomised, placebo-

(56) References Cited

OTHER PUBLICATIONS controlled study. Lancet Neurol, http://neurology.thelancet.com. Published online Jan. 20, 2006 DOI:10.1016/S1474-4422(06)70327-1. 8 pages.

Filippi et al., (2010) The contribution of MRI in assessing cognitive impairment in multiple sclerosis. Neurology 75(23): 2121-2128.

Fisher et al., (2008) Gray matter atrophy in multiple sclerosis: a longitudinal study. Ann Neurol 64(3): 255-265.

Tysabri@ Product Label (Oct. 2008) Elan Pharmaceuticals, Inc., 30 pages.

U.S. Dep't Health & Human Servs., Common Terminology Criteria for Adverse Events (CTCAE) (Published: May 28, 2009 (v4.03: Jun. 14, 2010)). 196 pages.

Valeant Pharms. Int'l, Inc., Transcript of Jun. 17, 2014 Investor Presentation, http://1.usa.gov/21PTRZK.

Valenzuela et al., (2007) Clinical response to glatiramer acetate correlates with modulation of IFN-γ and IL-4 expression in multiple sclerosis. Mult Scler 13(6): 754-762.

Van Metre et al., (1996) Pain and dermal reaction caused by injected glycerin in immunotherapy solutions. J Allergy Clin Immunol 97(5): 1033-1039.

Varkony et al., (2009) The glatiramoid class of immunomodulator drugs. Expert Opin Pharmacother 10(4): 657-668.

Viglietta Vet al., (2004) Loss of functional suppression by CD4+ CD25+ regulatory T cells in patients with multiple sclerosis. J Exp Med 199(7): 971-979.

Virley (2005) Developing therapeutics for the treatment of multiple sclerosis. NeuroRx 2(4): 638-649.

Weber et al., (2004) Multiple sclerosis: glatiramer acetate inhibits monocyte reactivity in vitro and in vivo. Brain 127(Pt 6): 1370-1378.

Weber et al., (2007) Mechanism of action of glatiramer acetate in treatment of multiple sclerosis. Neurotherapeutics 4(4): 647-653.

Webster's Ninth New Collegiate Dictionary, Merriam-Webster, Inc., 1985, p. 872, submitted as Exhibit 2027 in Inter Partes Review Case No. IPR2015-00830.

Wekerle et al., (1986) Cellular immune reactivity within the CNS. Trends in Neurosciences 9: 271-277.

Wolinsky (2004) Glatiramer acetate for the treatment of multiple sclerosis. Expert Opin Pharmacother 5(4): 875-891.

Wolinsky (2006) The use of glatiramer acetate in the treatment of multiple sclerosis. Adv Neurol 98: 273-292. Abstract.

Wolinsky et al., (2009) Glatiramer acetate treatment in PPMS: why males appear to respond favorably. J Neurol Sci 286(1-2): 92-98.

Wroblewski (1991) Mechanism of deiodination of 125I-human growth hormone in vivo. Relevance to the study of protein disposition. Biochem Pharmacol 42(4): 889-897.

Wynn et.al., Patient Experience with Glatiramer Acetate 40 mg/1 ml Three-Times Weekly Treatment for Relapsing-Remitting Multiple Sclerosis: Results from the GLACIER Extension Study. Neurology 84 (14 Supplement): P7.218. Presented at The 8th Congress of the Pan-Asian Committee for Treatment and Research in Multiple Sclerosis, Seoul, Republic of Korea (Nov. 19-21, 2015) 1 page.

Yong (2002) Differential mechanisms of action of interferon-beta and glatiramer aetate in MS. Neurology 59(6): 802-808.

Zellner et al., (2005) Quantitative validation of different protein precipitation methods in proteome analysis of blood platelets. Electrophoresis 26(12): 2481-2489.

Zhang and Hay (2014a) Cost-effectiveness of Fingolimod, Teriflunomide, Dimethyl Fumarate and Intramuscular Interferon Beta-1a in Relapsing-remitting Multiple Sclerosis. Poster, Monday Morning, PND20, ISPOR 19th Annual International Conference, May 2014, Montreal, Quebec, Canada, 1 page.

Zhang and Hay (2014b) Cost-effectiveness of Fingolimod, Teriflunomide, Dimethyl Fumarate and Intramuscular Interferon Beta-1a in Relapsing-remitting Multiple Sclerosis. American Society for Health Economics 5th Biennial Conference, Jun. 2014, Los Angeles, CA, 1 page.

Zhang et al., (2015) Cost effectiveness of fingolimod, teriflunomide, dimethyl fumarate and intramuscular interferon-31a in relapsing-remitting multiple sclerosis. CNS Drugs 29(1): 71-81.

Ziemssen (2005) Modulating processes within the central nervous system is central to therapeutic control of multiple sclerosis. J Neurol 252 Suppl 5: v38-v45.

Ziemssen and Gilgun-Sherki (2015) Sub-analysis of geographical variations in the 2-year observational COPTIMIZE trial of patients with relapsing-remitting multiple sclerosis converting to glatiramer acetate. BMC Neurol 15: 189.

Ziemssen and Schrempf (2007) Glatiramer acetate: mechanisms of action in multiple sclerosis. Int Rev Neurobiol 79: 537-570.

Ziemssen et al., (2001) Risk-benefit assessment of glatiramer acetate in multiple sclerosis. Drug Saf 24(13): 979-990.

Ziemssen et al., (2002) Glatiramer acetate-specific T-helper 1-and 2-type cell lines produce BDNF: implications for multiple sclerosis therapy. Brain-derived neurotrophic factor. Brain 125(Pt 11): 2381-2391.

Ziemssen et al., (2008) Effects of glatiramer acetate on fatigue and days of absence from work in first-time treated relapsing-remitting multiple sclerosis. Health Qual Life Outcomes 6: 67, 6 pages.

Ziemssen et al., (2008) Presence of Glatiramer Acetate-Specific TH2 Cells in the Cerebrospinal Fluid of Patients with Multiple Sclerosis 12 Months After the Start of Therapy with Glatiramer Acetate, J Neurodegen Regen 1: 19-22.

Ziemssen et al., (2014) A 2-year observational study of patients with relapsing-remitting multiple sclerosis converting to glatiramer acetate from other disease-modifying therapies: the COPTIMIZE trial. J Neurol 261(11): 2101-2111.

Ziemssen et al., (2014) QualiCOP: An Open-Label, Prospective, Observational Study of Glatiramer Acetate in Patients with Relapsing-Remitting Multiple Sclerosis. Retrieved form: http://www.comtecmed.com/cony/2014/Uploads/Editor/Rainer.pdf, 1 page.

Ziemssen T. (2004) Neuroprotection and Glatiramer Acetate: The Possible Role in the Treatment of Multiple Sclerosis. In: Vécsei L. (eds) Frontiers in Clinical Neuroscience. Advances in Experimental Medicine and Biology, vol. 541., pp. 111-134. Springer, Boston, MA. https://doi.org/10.1007/978-1-4419-8969-7_7.

Zivadinov et al., (2008) Mechanisms of action of disease-modifying agents and brain volume changes in multiple sclerosis. Neurology 71(2): 136-144.

Zivadinov et al., (2015) MRI indicators of brain tissue loss: 3-year results of the Glatiramer Acetate Low-frequency Administration (GALA) open-label extension study in relapsing-remitting multiple sclerosis (P7.255). Neurology 84 (14 Supplement): P7.255. Presented at The American Academy of Neurology 2015 Annual Meeting, Washington, DC (Apr. 18-25, 2015) 1 page.

Bala et al., (2004) PLGA nanoparticles in drug delivery: the state of the art. Critical Reviews™ in Therapeutic Drug Carrier Systems 21(5): 387-422.

Tiwari and Verma (2011) Microencapsulation technique by solvent evaporation method (Study of effect of process variables). Int J of Pharm & Life Sci (IJPLS) 2(8): 998-1005.

O'Donnell and McGinity (1997) Preparation of microspheres by the solvent evaporation technique. Adv Drug Deliv Rev 28(1): 25-42.

Abate et al., Air-Bubble-triggered drop formation in microfluidics, Lab Chip, 2011, 11, 1713-1716.

Oraceska et al., "A comparison of dissolution properties from matrix tablets prepared from microcapsules and mixtures containing phenobarbitone and poly(DL-lactic acid)". In: Pharmaceutical Technology, Controlled Drug Release. Wells JI and Rubinstein MH (eds.). Taylor & Francis e-Library, 2005, pp. 141-151.

Polman et al., (2011) Diagnostic criteria for multiple sclerosis: 2010 Revisions to the McDonald criteria. Ann Neurol 69(2): 292-302.

Racke and Lovett-Racke (2011) Glatiramer acetate treatment of multiple sclerosis: an immunological perspective. J Immunol 186(4): 1887-1890.

Ramot et al., (2016) Biocompatibility and safety of PLA and its copolymers. Adv Drug Deliv Rev 107: 153-162.

Ravivarapu et al., "Biodegradable Polymeric Delivery Systems". In: Design of Controlled Release Drug Delivery Systems. Li X and Jasti BR (eds.). McGraw-Hill Chemical Engineering, 2006, pp. 271-303.

(56) References Cited

OTHER PUBLICATIONS

Reagan-Shaw et al., (2008) Dose translation from animal to human studies revisited. FASEB J 22(3): 659-661.
Rotstein et al., (2015) Evaluation of no evidence of disease activity in a 7-year longitudinal multiple sclerosis cohort. JAMA Neurol 72(2): 152-158.
Ruggieri et al., (2007) Glatiramer acetate in multiple sclerosis: a review. CNS Drug Rev 13(2): 178-191.
Sabatos-Peyton et al., (2010) Antigen-specific immunotherapy of autoimmune and allergic diseases. Curr Opin Immunol 22(5): 609-615.
Sayed et al., (2011) Cutting edge: mast cells regulate disease severity in a relapsing-remitting model of multiple sclerosis. J Immunol 186(6): 3294-3298.
Sela et al., (1990) Suppressive activity of Cop-1 in EAE and its Relevance to Multiple Sclerosis. Bull. Inst. Pasteur (Paris) 88: 303-314.
Shenoy et al., (2002) Poly(DL-lactide-co-glycolide) microporous microsphere-based depot formulation of a peptide-like antineoplastic agent. J Microencapsul 19(4): 523-535.
Sorensen et al., (1998) Intravenous immunoglobulin G reduces MRI activity in relapsing multiple sclerosis. Neurology 50(5): 1273-1281.
Stern et al., (2008) Amino acid copolymer-specific IL-10-secreting regulatory T cells that ameliorate autoimmune diseases in mice. Proc Natl Acad Sci USA 105(13): 5172-5176.
Tabansky et al., (2015) Advancing drug delivery systems for the treatment of multiple sclerosis. Immunol Res 63(1-3): 58-69.
Teitelbaum et al., (1971) Suppression of experimental allergic encephalomyelitis by a synthetic polypeptide. Eur J Immunol 1(4): 242-248.
Teitelbaum et al., (1973) Suppression by several synthetic polypeptides of experimental allergic encephalomyelitis Induced in guinea pigs and rabbits with bovine and human basic encephalitogen. Eur J Immunol 3(5): 273-279.
Teitelbaum et al., (1974) Suppression of experimental allergic encephalomyelitis in rhesus monkeys by a synthetic basic copolymer. Clin. Immunol. Immunopathol. 3(2): 256-262.
Teitelbaum et al., (1977) Suppression of experimental allergic encephalomyelitis in baboons by Cop 1. Israeli Med Sci 13: 1038.
Teitelbaum et al., (1988) Specific inhibition of the T-cell response to myelin basic protein by the synthetic copolymer Cop 1. Proc Natl Acad Sci USA 85(24): 9724-9728.
Teitelbaum et al., (1996) Copolymer 1 inhibits chronic relapsing experimental allergic encephalomyelitis induced by proteolipid protein (PLP) peptides in mice and interferes with PLP-specific T cell responses. J Neuroimmunol 64(2): 209-217.
Teitelbaum et al., (2003) Antibodies to glatiramer acetate do not interfere with its biological functions and therapeutic efficacy. Mult Scler 9(6): 592-599.
Thall and Russell (1998) A strategy for dose-finding and safety monitoring based on efficacy and adverse outcomes in phase I/II clinical trials. Biometrics 54(1): 251-264.
Webb et al., (1973) Correlation between strain differences in susceptibility to experimental allergic encephalomyelitis and the immune response to encephalitogenic protein in inbred guinea pigs. Immunol Commun 2(2): 185-192.

Wolinsky and PROMiSe Trial Study Group (2004) The PROMiSe trial: baseline data review and progress report. Mult Scler 10 Suppl 1: S65-S72.
Wolinsky et al., (2007) Glatiramer acetate in primary progressive multiple sclerosis: results of a multinational, multicenter, double-blind, placebo-controlled trial. Ann Neurol 61(1): 14-24.
Wolinsky et al., (2015) GLACIER: An open-label, randomized, multicenter study to assess the safety and tolerability of glatiramer acetate 40 mg three-times weekly versus 20 mg daily in patients with relapsing-remitting multiple sclerosis. Mult Scler Relat Disord 4(4): 370-376.
Ziemssen et al., (2015) Evaluation of Study and Patient Characteristics of Clinical Studies in Primary Progressive Multiple Sclerosis: A Systematic Review. PLoS One 10(9): e0138243; 22 pages.
Clinical Trials, NCT02212886, Jan. 6, 2016, Retrieved from the Internet: https://clinicaltrials.gov/ct2/history/NCT02212886?V_9=View#StudyPageTop. 5 pages.
ClinicalTrials.gov Identifier: NCT02212886. Safety, Tolerability and Efficacy of Monthly Long-acting IM Injection of 80 or 40 mg GA Depot in Subjects With RRMS. Retrieved form: https://clinicaltrials.gov/ct2/show/NCT02212886?term=mi+ga+depot++001&rank=1 on Aug. 10, 2016. 7 pages.
COPAXONE®, Highlights of prescribing information; COPAXONE (glatiramer acetate) solution for subcutaneous Injection, Initial U.S. Approval: 1996. Revised: Feb. 2009 (Feb. 2009). Marketed by: TEVA Neuroscience, Inc., Kansas City, MO, USA. 22 pages.
COPAXONE®, Highlights of prescribing information; COPAXONE (glatiramer acetate injection) for subcutaneous use, Initial U.S. Approval: 1996. Revised: Aug. 2016 (Aug. 2016). Marketed by: Teva Neuroscience, Inc., Overland Park, KS, USA. 8 pages.
Expanded Disability Status Scale, from https://www.mssociety.org.uk/about-ms/treatments-and-therapies/getting-treatment-for-ms . . . , pp. 1-7, accessed Sep. 20, 2021.
NCT02212886, from https://clinicaltrials.gov/ct2/history/NCT02212886?V_7=View, Dec. 23, 2015, retrieved on Sep. 21, 2021, 10 pages.
NCT02212886, Jun. 1, 2016. Retrieved from the Internet: URL: https://clinicaltrials.gov/ct2/history/NCT02212886?V_10=View#StudyPageTop [retrieved on Jul. 13, 2021]. 7 pages.
OCREVUSTM (ocrelizumab) injection, for intravenous use Initial U.S. Approval: 2017; Revised: Mar. 2017. Reference ID: 4076448.
OCREVUSTM [ocrelizumab], Manufactured by: Genentech, Inc. South San Francisco, CA, USA. The Medication Guide has been approved by the U.S. Food and Drug Administration. 18 pages.
Safety, Tolerability and Efficacy of Monthly Long-acting IM Injection of 80 or 40 mg GA Depot in Subjects With RRMS—Tubular view—ClinicalTrials.gov. Aug. 8, 2014 (Aug. 8, 2014), XP055679718. Retrieved from the Internet: URL: https://clinicaltrials.gov/ct2/show/record/NCT02212886, on Mar. 25, 2020. 4 pages.
U.S. FDA grants Breakthrough Therapy Designation for Roche's investigational medicine ocrelizumab in primary progressive multiple sclerosis; Investor Update. Basel, Feb. 17, 2016. Retrieved from: https://www.roche.com/investors/updates/inv-update-2016-02-17.htm on Aug. 29, 2019. 4 pages.
Junichi Kira (2016) Latest Multiple Sclerosis Treatment. Journal of the Japanese Society of Internal Medicine 105(5): 894-904. With machine English translation of details and abstract.

\* cited by examiner

PROCESS FOR PREPARING MICROPARTICLES CONTAINING GLATIRAMER ACETATE

CROSS REFERENCE TO RELATED APPLICATION(S)

This application is continuation of U.S. application Ser. No. 16/328,572 filed Feb. 26, 2019, is now U.S. Pat. No. 11,471,421, which is a 35 U.S.C. 371 National Phase Entry Application from PCT/IL2017/050954, filed Aug. 28, 2017, which claims the benefit of US Provisional Patent Application No. 62/380,426 filed on Aug. 28, 2016; and is continuation of U.S. application Ser. No. 16/328,582 filed Feb. 26, 2019, which is a 35 U.S.C. 371 National Phase Entry Application from PCT/IL2017/050882, filed Aug. 9, 2017, which claims the benefit of US Provisional Patent Application No. 62/381,598 filed on Aug. 31, 2016, the disclosures of which are incorporated herein in their entirety by reference.

FIELD OF THE INVENTION

The present invention relates to an improved process for preparing microparticles containing glatiramer acetate having low levels of residual organic solvent(s), in particular dichloromethane (DCM). The microparticles are incorporated into long acting parenteral pharmaceutical compositions in depot form that are suitable for subcutaneous or intramuscular implantation or injection, and that may be used to treat multiple sclerosis.

BACKGROUND OF THE INVENTION

Glatiramer acetate (GA), marketed under the tradename Copaxone®, is indicated for the treatment of patients with relapsing-forms of multiple sclerosis. Glatiramer acetate is a random polymer composed of four amino acids that are found in myelin basic protein. Glatiramer acetate comprises the acetate salts of polypeptides containing L-glutamic acid, L-alanine, L-tyrosine and L-lysine. The average molar fractions of the amino acids are 0.141, 0.427, 0.095 and 0.338, respectively, and the average molecular weight of copolymer-1 is between 5,000 and 9,000 daltons. Chemically, glatiramer acetate is designated L-glutamic acid polymer with L-alanine, L-lysine and L-tyrosine, acetate (salt). Its structural formula is: (Glu, Ala, Lys, Tyr)x$CH_3COOH$, approx. ratio $Glu_{14}Ala_{43}Tyr_{10}Lyz_{34}x(CH_3COOH)_{20}$.

Copaxone® is manufactured as a solution for subcutaneous injection. Each 1 mL of Copaxone® solution contains 20 mg or 40 mg of glatiramer acetate and 40 mg of mannitol. The 20 mg/mL strength is indicated for daily injection, while the 40 mg/mL strength is indicated for injection three times per week. Side effects generally include a lump at the injection site (injection site reaction), aches, fever, and chills.

U.S. Pat. Nos. 8,377,885 and 8,796,226 describe long acting parenteral compositions of pharmaceutically acceptable salts of glatiramer, including glatiramer acetate, in depot form suitable for subcutaneous or intramuscular implantation or injection. The long acting compositions provide equal or superior therapeutic efficacy compared with daily injectable Copaxone® formulations, with reduced incidence and/or severity of side effects such as injection site irritation, due to the reduced frequency of administration. The compositions are prepared by a "double emulsification" process. An aqueous solution of glatiramer acetate is dispersed in a solution of a biodegradable polymer (PLGA) in a volatile water-immiscible organic solvent. The obtained "water-in-oil (w/o) emulsion" is dispersed in a continuous external water phase containing surfactant to form "water-in oil-in water (w/o/w) double emulsion" droplets. The organic solvent is slowly evaporated by stirring the double emulsion in a fume hood. The resulting microparticles are collected by filtration or centrifugation, washed with water and lyophilized. The solvents used in the aforementioned process are halogenated hydrocarbons, particularly chloroform or dichloromethane, which act as solvents for the polymer. The presence of residual, but detectable, halogenated hydrocarbon solvents in the final product, however, is undesirable, because of their general toxicity and possible carcinogenic activity. To address this, regulatory agencies have imposed limitations on the amount of residual organic solvents present in pharmaceutical compositions intended for human and veterinary uses.

There is a need in the art for an improved and reliable process for preparing microparticles containing glatiramer acetate having low levels of residual organic solvent(s), in particular halogenated organic solvents.

SUMMARY OF THE INVENTION

The present invention provides an improved process for preparing microparticles containing glatiramer acetate having low levels of residual organic solvent(s), in particular halogenated hydrocarbons such as dichloromethane. Unexpectedly it has been discovered that organic solvent levels may be reduced to regulatory-acceptable levels (e.g., less than about 600 ppm for dichloromethane) by altering the organic solvent evaporation step in the double emulsification process previously described in U.S. Pat. Nos. 8,377,885 and 8,796,226. A main challenge in modifying said process was to keep the microparticle's morphology, the binding percentage and the release profile of the glatiramer acetate active ingredient intact, despite the process modifications. It has now been discovered that application of vacuum and/or air stream to the double water-in-oil-in-water double emulsion results in a product having reduced levels of organic solvent, while still maintaining intact microparticles of glatiramer acetate. In particular, by careful adjustment of the mixing, air bubbling and/or vacuum intensities, microparticles were achieved having desired morphological and therapeutic properties (e.g., drug release profile), while at the same time minimizing the level of organic solvent to regulatory acceptable levels. For example, for chlorinated organic solvents such as dichloromethane (DCM, also referred to interchangeably as methylene chloride), the regulatory limits according to ICH guidelines are 600 ppm.

Thus, the present invention provides a process for preparing microparticles comprising glatiramer acetate, the process comprising the steps of: (a) preparing an internal aqueous phase comprising glatiramer acetate and water; (b) preparing an organic phase comprising a biodegradable or non-biodegradable polymer and a water-immiscible volatile organic solvent; (c) preparing an external aqueous phase comprising water and a surfactant; (d) mixing the internal aqueous phase obtained in step (a) and the organic phase obtained in step (b) to form a water-in-oil (w/o) emulsion; (e) mixing the water-in-oil (w/o) emulsion obtained in step (d) with the external water phase obtained in step (c) to obtain a water-in-oil-in-water (w/o/w) double emulsion; (f) removing the organic solvent by mixing the water-in-oil-in-water (w/o/w) double emulsion obtained in step (e), and applying an air stream and/or a vacuum; and (g) drying to obtain microparticles of glatiramer acetate, the microparticles comprising less than about 1,000 ppm of residual organic solvent. In one embodiment, step (f) is conducted under conditions sufficient to reduce the level of organic solvent to less than about 1,000 ppm, preferably less than about 600 ppm.

As contemplated herein, the process of the present invention results in a product having reduced levels of residual organic solvent(s), thereby being compliant with regulatory imposed limitations. In one embodiment, the microparticles comprise less than about 600 ppm residual organic solvent, which is the regulatory limit for chlorinated solvents such as DCM according to ICH guidelines. In another embodiment, the microparticles comprise less than about 500 ppm residual organic solvent. In another embodiment, the microparticles comprise less than about 250 ppm residual organic solvent. In yet another embodiment, the microparticles comprise less than about 100 ppm of residual organic solvent.

In other embodiments, the microparticles comprise less than about 0.1% of residual organic solvent(s). In another embodiment, the microparticles comprise less than about 0.05% residual organic solvent(s). In yet another embodiment, the microparticles comprise less than about 0.01% of residual organic solvent(s).

The organic solvent used in the process of the invention is water-immiscible and volatile. In some currently preferred embodiments, the organic solvent is a halogenated organic solvent such as a halogenated hydrocarbon. In some currently preferred embodiments, the chlorinated hydrocarbon is dichloromethane or chloroform, with each possibility representing a separate embodiment of the present invention.

In one particular embodiment, the process of the invention utilizes dichloromethane as an organic solvent. In accordance with this embodiment, the resulting microparticles comprise less than about 600 ppm, preferably less than about 500 ppm, less than about 250 ppm or less than about 100 ppm of residual dichloromethane.

The solvent removal step (f) comprises a combination of mixing and application of an air stream and/or vacuum to the water-in-oil-in-water (w/o/w) double emulsion. The mixing, application of air stream and/or vacuum are conducted under suitable conditions that will not affect that integrity of the final product (e.g., its morphology, GA binding percentage or release profile), while still giving rise to a product having low levels of organic solvent, as described herein.

In some embodiments, the w/o/w double emulsion may be mixed using a homogenizer, preferably at a speed of at least about 2,500 rounds per minute (RPM), preferably at least about 2,750 RPM. In some embodiments, step (f) comprises mixing the w/o/w double emulsion in combination with application of a vacuum. Preferably, the vacuum is applied for at least about 3 hours, or at least about 5 hours. In other embodiments, step (f) comprises mixing of the w/o/w double emulsion in combination with applying a compressed air stream to the w/o/w double emulsion at a pressure of about 0.1 to 1 bar, preferably about 0.5 bar or any value inbetween. In yet other embodiments, step (f) comprises mixing of the w/o/w double emulsion together with applying a combination of compressed air stream and vacuum as described above.

After solvent evaporation, the glatiramer acetate microparticles are isolated by drying (step (g)). In some embodiments, this step comprises drying the obtained microparticles into bulk or unit dose preparation. The drying may be performed by any method known in the art, for example lyophilization or freeze-drying or any other suitable drying method. In other embodiments, the process further includes a step of filtering or centrifuging the product of step (f), optionally washing with water, prior to drying, thereby obtaining the microparticles of glatiramer acetate. The polymer used in the organic phase may be biodegradable or non-biodegradable. In some embodiments, the biodegradable or non-biodegradable polymer is selected from the group consisting of poly(D,L, lactic acid) (PLA), polyglycolides (PGA), poly(lactide-co-glycolide) (PLGA) polycaprolactone, polyhydroxybutyrate, polyorthoesters, polyalkaneanhydrides, gelatin, collagen, oxidized cellulose, and polyphosphazene, with each possibility representing a separate embodiment of the present invention. In some currently preferred embodiments, the polymer is a biodegradable polymer selected from the group consisting of PLA, PGA and PLGA. A currently preferred biodegradable polymer is PLGA.

In additional embodiments, the external aqueous phase comprises a surfactant selected from polyvinyl alcohol (PVA), partially hydrolyzed polyvinyl alcohol (PVA), polysorbate, polyethylene oxide-polypropylene oxide block copolymers and cellulose esters. Each possibility represents a separate embodiment of the invention. In a currently preferred embodiments, the surfactant is PVA or partially hydrolyzed PVA.

In further embodiments, the composition further comprises a tonicity modifier. A preferred tonicity modifier is sodium chloride which is added to one or more of the aqueous phases, for creation of osmotic balance. Other suitable tonicity modifiers are described in the detailed description hereinbelow.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

According to other embodiments, the glatiramer acetate or other pharmaceutically acceptable salt of glatiramer comprises about 15 to about 100 amino acids.

In some embodiments the microparticles comprise from about 20 mg to about 750 mg glatiramer acetate. In other embodiments, the microparticles comprise about 40 mg glatiramer acetate. In other embodiments, the microparticles comprise about 80 mg glatiramer acetate.

As contemplated herein, the glatiramer acetate microparticles are prepared in the form of a depot formulation, suitable for subcutaneous or intramuscular implantation at a medically acceptable location in a subject in need thereof. Thus, in some embodiments, the present invention relates to a long acting parenteral pharmaceutical composition comprising a therapeutically effective amount of glatiramer acetate, the composition being in a sustained release depot form suitable for subcutaneous or intramuscular implantation at a medically acceptable location in a subject in need thereof, the composition comprising microparticles of glatiramer acetate prepared in accordance with the process of the invention.

According to some embodiments, the long acting depot is suitable for a dosing schedule from about once weekly to about once in every 6 months. According to particular embodiments, the composition is suitable for dosing from about once every 2 weeks to about once monthly.

According to other embodiments, the long acting depot releases a therapeutically effective amount of glatiramer acetate over a period of about 1 week to about 6 months. According to other embodiments, the long acting depot releases a therapeutically effective amount of glatiramer acetate over a period of about 2 weeks to about 1 month. Specific examples of the long acting compositions include biodegradable or non-biodegradable microspheres, implants of any suitable geometric shape, implantable rods, implantable capsules, implantable rings, prolonged release gels and erodible matrices. Each possibility represents a separate embodiment of the invention.

The present invention further provides a method of treating multiple sclerosis, comprising the parenteral administration or implantation of a depot composition comprising a therapeutically effective amount of glatiramer acetate, the composition being prepared in accordance with the process of the present invention.

Advantageously, the pharmaceutical compositions provide equal or superior therapeutic efficacy to the commercially available daily injectable dosage forms, with reduced incidence and/or severity of side effects at the local and/or systemic levels.

The present invention encompasses a composition comprising glatiramer acetate in depot form prepared by the process according to the present invention, the depot formulation being suitable for implantation into an individual in need thereof, for use in treating multiple sclerosis, in particular relapsing-remitting multiple sclerosis (RRMS).

The present invention further encompasses the use of the implantable depot of glatiramer acetate prepared in accordance with the process of the present invention, the depot being suitable for providing prolonged release or prolonged action of glatiramer in a subject.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides an improved process for preparing microparticles containing glatiramer acetate having low levels of residual organic solvent(s), in particular dichloromethane. The microparticles are in the form of a depot formulation which may be administered by parenteral administration (e.g., intramuscularly or subcutaneously), and affords equal or superior therapeutic efficacy compared with daily Copaxone® injections and thus result in improved patient compliance. In addition to providing similar therapeutic efficacy and reduced side effects, the long acting depot compositions contain low levels or residual organic solvent (e.g., dichloromethane), thereby complying with regulatory requirements regarding permitted residual amounts of such solvents.

The microparticulate compositions of the present invention comprise a water-in oil-in water (w/o/w) double emulsion. The double emulsion comprises an internal aqueous phase comprising glatiramer acetate, an oil phase or water-immiscible organic phase comprising a biodegradable or non-biodegradable polymer and a water-immiscible organic solvent, and an external aqueous phase comprising a surfactant and optionally a tonicity modifier. The terms "oil phase" and "water-immiscible organic phase" may be used interchangeably herein.

Preparation of Microparticles

The compositions of the present invention can be prepared in the form of injectable microparticles by a process known as a "double emulsification" process, which represents an improvement of the process described in U.S. Pat. Nos. 8,377,885 and 8,796,226. According to the principles of the present invention, a solution of glatiramer acetate is dispersed in a solution of a biodegradable or non-biodegradable polymer in water-immiscible volatile organic solvent. The thus obtained "water-in-oil (w/o) emulsion" is then dispersed in a continuous external water phase containing surfactant to form "water-in oil-in water (w/o/w) double emulsion" droplets. The organic solvent is then removed (i.e., evaporated) by mixing the water-in-oil-in-water (w/o/w) double emulsion and applying an air stream and/or a vacuum, under conditions sufficient to reduce the amount of organic solvent to levels acceptable for pharmaceutical applications (e.g., compliance with ICH guidelines). The process described in U.S. Pat. Nos. 8,377,885 and 8,796,226 does not contemplate application of an air stream or a vacuum during the solvent evaporation step. In some embodiments, the level of residual organic solvent is reduced to less than the maximal residual solvent permitted according to regulatory agencies. Generally, the level of residual organic solvent is reduced to less than about 1,000 ppm. When halogenated organic solvents (e.g., dichloromethane) are used, the level is preferably reduced to less than about 600 ppm, which is the maximal regulatory allowed level. After evaporation of the organic solvent, the microparticles solidify and are collected by filtration or centrifugation. The collected microparticles (MPs) are washed with purified water to eliminate most of the surfactant and non-bonded peptide and centrifuged again. The washed MPs are collected and lyophilized without additives or with the addition of cryoprotectant (e g, mannitol) to facilitate their subsequent reconstitution. Surprisingly, utilizing the process of the present invention, glatiramer acetate microparticles are obtain that retain the microparticles' desired properties such as morphology, binding percentage ("potency") and release profile, while still achieving reduced levels of organic solvents.

According to the present invention, glatiramer acetate microparticles are prepared by a process comprising the steps of: (a) preparing an internal aqueous phase comprising glatiramer acetate and water; (b) preparing an organic phase comprising a biodegradable or non-biodegradable polymer and a water-immiscible volatile organic solvent; (c) preparing an external aqueous phase comprising water and a surfactant; (d) mixing the internal aqueous phase obtained in step (a) and the organic phase obtained in step (b) to form a water-in-oil (w/o) emulsion; (e) mixing the water-in-oil (w/o) emulsion obtained in step (d) with the external water phase obtained in step (c) to obtain a water-in-oil-in-water (w/o/w) double emulsion; (f) removing the organic solvent by mixing the water-in-oil-in-water (w/o/w) double emulsion obtained in step (e), and applying an air stream and/or a vacuum; and (g) drying to obtain microparticles of glatiramer acetate, the microparticles comprising less than about 1,000 ppm, preferably less than 600 ppm of residual organic solvent. In one embodiment, step (f) is conducted under conditions sufficient to reduce the level of organic solvent to less than about 1,000 ppm, preferably less than about 600 ppm.

Internal Water Phase

The internal aqueous (water) phase comprises glatiramer acetate and water, which is preferably sterile water for injection (WFI). A suitable concentration range of glatiramer acetate in the internal water phase is between about 10 mg/mL to about 150 mg/mL, or any amount in-between. For example, glatiramer acetate concentration in the internal water phase may be between 80 and 120 mg/mL, between 90 and 110 mg/mL, and so forth.

For preparation of the internal water phase, a solution containing sterile WFI and glatiramer acetate is prepared and optionally filtered.

Organic Phase (Water-Immiscible Phase)

The organic phase comprises a biodegradable or non-biodegradable polymer and an organic solvent. The organic solvent is water-immiscible and volatile. In some currently preferred embodiments, the organic solvent is a halogenated hydrocarbon. In some embodiments, the halogenated solvent is a chlorinated solvent, for example dichloromethane or chloroform. Dichloromethane is also referred to interchangeably as dichloromethane or DCM. Each possibility represents a separate embodiment of the present invention.

In one particular embodiment, the process of the invention utilizes dichloromethane as an organic solvent. Regulatory allowed amounts of this solvent in pharmaceutical compositions are about 600 ppm. Accordingly, the microparticles resulting from the process of the invention preferably comprise less than about 600 ppm dichloromethane. In preferred embodiments, the resulting microparticles comprise less than about 500 ppm, for example less than about 250 ppm or less than about 100 ppm of residual dichloromethane. Each possibility represents a separate embodiment of the present invention.

The polymer may be a biodegradable or non-biodegradable polymer, with preference given to biodegradable polymers. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-[carboxyphenoxy]propane), CPP; poly(p-{carboxyphenoxy}hexane)s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof. Each possibility represents a separate embodiment of the present invention.

In some embodiments, the microparticles comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. In other embodiments, the microparticles comprise a biodegradable polymer selected from, but not limited to, PLGA, PLA and PGA. Each possibility represents a separate embodiment of the present invention.

A currently preferred biodegradable polymer is a lactic acid-based polymer, more preferably polylactide, or poly (D,L-lactide-co-glycolide) i.e. PLGA. Preferably, the biodegradable polymer is present in an amount between about 10% to about 98% w/w of the composition. The lactic acid-based polymer has a monomer ratio of lactic acid to glycolic acid in the range of 100:0 to about 0:100, preferably about 100:0 to about 10:90 and has an average molecular weight of from about 1,000 to about 200,000 daltons. However, it is understood that the amount of biodegradable polymer is determined by parameters such as the duration of use and the like.

PLGA polymers are commercially available from multiple suppliers; Alkermes (Medisorb polymers), Absorbable Polymers International [formerly Birmingham Polymers (a Division of Durect)], Purac and Boehringer Ingelheim.

For preparation of the internal water phase, the organic solvent and polymer are mixed and optionally filtered.

External Water Phase

The external water phase comprises water and a surfactant. The water is preferably sterile WFI. The external water phase may further comprise a tonicity modifier, for maintenance of osmotic balance. A preferred tonicity modifier is sodium chloride which is added to the external water phase. Other suitable tonicity modifiers include, but are not limited to: mannitol and glucose. Each possibility represents a separate embodiment of the invention.

The surfactant in the external water phase is preferably polyvinyl alcohol (PVA). However, other surfactants can be used, for example polysorbate, polyethylene oxide-polypropylene oxide block copolymers or cellulose esters, or any of the co-surfactants described hereinbelow.

For preparation of the external water phase (step (c)), the surfactant and optional tonicity modifier are mixed in water, preferably sterile WFI, and optionally filtered. Alternatively, a solution of surfactant in water may be dispersed or dissolved in a solution of water comprising a tonicity modifier. In one embodiment of the present invention, the external water phase was prepared by preparing a partially hydrolyzed PVA solution in sterile WFI and filtering through a membrane. Separately, a solution of NaCl was prepared in sterile WFI and filtered through a membrane. The NaCl solution was added to the PVA solution to thereby form the external water phase.

Water-In-Oil (w/o) Emulsion Preparation

After preparing each of the aqueous and organic phases, the w/o emulsion is formed. For this, the internal aqueous phase and organic phase are mixed, optionally using a homogenizer or other high shear mixing method, under conditions sufficient to form the w/o emulsion. In one embodiment, the internal water phase was added to the organic phase and processed using a homogenizer equipped with a rotor stator dispersion device at 2,500-10,000 rounds per minute (RPM) for a time period ranging from 1 to 30 minutes. In one specific embodiment, the w/o emulsion was prepared by homogenizing at 7,200 RPM for 10 minutes (high shear mixing).

Water-In-Oil-In-Water (w/o/w) Double Emulsion Preparation

Next, the w/o emulsion is mixed with the external water phase to form a water-in-oil-in-water (w/o/w) double emulsion. The mixing can occur using a homogenizer or other high shear mixing method, and can be performed in one batch or in multiple batches. For example, the w/o emulsion can be added to a portion of the external water phase followed by mixing, followed by adding the rest of the external water phase. Mixing is performed as described above for the w/o emulsion. In one embodiment, the w/o/w emulsion was prepared by adding the w/o emulsion to half of the external water phase during continuous mixing of the emulsion. The w/o/w double emulsion was processed using a homogenizer equipped with a rotor stator dispersion device at 2,500-10,000 rounds per minute (RPM) for a time period ranging from 1 to 30 minutes. In one specification embodiment, the w/o/w double emulsion was prepared by homogenizing a mixture containing half of the external water phase with the organic phase at 2,900 RPM for 3 minutes, followed by adding the rest of the external water phase (quench).

Solvent Removal/Evaporation

Next, the organic solvent is removed. The solvent removal step comprises a combination of mixing and application of an air stream and/or vacuum to the water-in-oil-in-water (w/o/w) double emulsion. The mixing, application of air stream and/or vacuum are conducted under suitable conditions that will not affect that integrity of the final product, and will give rise to a product having low levels of organic solvent, as described herein.

In some embodiments, the w/o/w double emulsion may be mixed using a homogenizer or other high shear mixing methods, preferably at a speed of at least about 2,500 RPM, preferably at least about 2,750 RPM. Higher or lower mixing speeds may be used, if desired.

In some embodiments, the solvent removal step comprises mixing of the w/o/w double emulsion in combination with application of vacuum. The vacuum may be applied for the desired amount of time to achieve the desired results, i.e., removal of solvent. For example, vacuum may be applied for at least 1 hour, at least 2 hours, preferably for at least about 3 hours, at least about 5 hours, etc. Vacuum may also be applied for longer amounts of time, e.g., 12-24 hours or overnight.

In other embodiments, the solvent removal step comprises mixing of the w/o/w double emulsion in combination with applying a compressed air stream to the w/o/w double emulsion. The air stream may be applied at a pressure of about 0.1 to 1 about bar, preferably about 0.5 bar. The air stream may be applied at a higher or lower pressure, depending on the desired outcome. The air pressure may be applied for the desired period of time, e.g., 1-24 hours, 5-24 hours, 10-20 hours, 10-12 hours, and the like.

In yet other embodiments, the solvent removal step comprises mixing of the w/o/w double emulsion and applying a combination of compressed air stream and vacuum.

In some specific embodiments, the w/o/w double emulsion was mixed using a homogenizer at different speeds for 15-17 hours. Compressed air was bubbled at 0.5 Pa through the emulsion for 10-12 hours. Vacuum was applied for the portion of the process, e.g., for about 3 hours or 5 about hours.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to about 100

Separation and Washing

After solvent evaporation, the glatiramer acetate microparticles are separated from the reaction mixture. In some embodiments, this step comprises filtering or centrifuging the suspension obtained from the solvent evaporation step. Centrifugation may be performed at any speed and time that will effectuate the separation of the microparticles from the emulsion. For example, in a non-limiting example, centrifugation may be performed at a speed of 2,500 to 10,000 RPM for a time period ranging, e.g., from 5 to 30 minutes. The obtained pellet may optionally be washed with water once or multiple times. In one specific embodiment, the suspension is centrifuged at 5,300 RPM for 10 minutes. The supernatant is discarded and the pellet (sedimented microparticles) is resuspended in WFI and mixed using a magnetic stirrer. The resuspended microparticles are again centrifuged at 2,900 RPM for 10 minutes to obtain glatiramer acetate microparticles.

Drying

The washed microparticles are then dried, e.g., by lyophilization/freeze drying or other drying methods known in the art, to obtain microparticles of glatiramer acetate in bulk or unit dose preparation. Drying is effectuated for a time period and at a temperature sufficient to remove the solvents and obtain dry microparticles. For example, lyophlization may occur at $-20°$ C. or below for a time period ranging from 12 to 48 hours.

As contemplated herein, the process of the present invention results in a product having reduced levels of residual organic solvent(s), thereby being compliant with regulatory imposed limitations. In one embodiment, the microparticles comprise less than about 600 ppm residual organic solvent. In one embodiment, the microparticles comprise less than about 500 ppm residual organic solvent. In another embodiment, the microparticles comprise less than about 250 ppm residual organic solvent. In yet another embodiment, the microparticles comprise less than about 100 ppm of residual organic solvent. In a preferred embodiment, the organic solvent is a halogenated organic solvent, for example a chlorinated organic solvent such as dichloromethane or chloroform. In this case, the microparticles should have no more than 600 ppm residual solvent, the maximal regulatory allowed amount.

Active Ingredient

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 5,000-9,000 daltons (FDA Copaxone® label) and the number of amino acid ranges between about 15 to about 100 amino acids. The term also refers to chemical derivatives and analogues of the compound.

Glatiramer acetate may be prepared and characterized as specified in any of U.S. Pat. Nos. 8,377,885; 8,796,226; 7,199,098; 6,620,847; 6,362,161; 6,342,476; 6,054,430; 6,048,898 and 5,981,589, the contents of each of these references are hereby incorporated in their entirety.

Depot Compositions

The microparticles prepared by the process of the present invention are preferably in the form of long acting parenteral pharmaceutical compositions comprising a therapeutically effective amount of glatiramer acetate, specifically in the form of a depot formulation suitable for subcutaneous or intramuscular implantation at a medically acceptable location in a subject in need thereof.

The term "parenteral" as used herein refers to routes selected from subcutaneous (SC), intravenous (IV), intramuscular (IM), intradermal (ID), intraperitoneal (IP) and the like.

The term "therapeutically effective amount" as used herein is intended to qualify the amount of glatiramer acetate copolymer that will achieve the goal of alleviation of the symptoms of multiple sclerosis. Suitable doses include, but are not limited to, 20-750 mg for each dosage form. However, it is understood that the amount of the glatiramer acetate copolymer administered will be determined by a physician, according to various parameters including the chosen route of administration, the age, weight, and the severity of the patient's symptoms. For example, the therapeutically effective amount of the glatiramer acetate may range from about 20-100 mg. In some embodiments, the therapeutically effective amount of glatiramer acetate in the depot formulation is 40 mg. In some embodiments, the therapeutically effective amount of glatiramer acetate in the depot formulation is 80 mg.

The term "long acting" as used herein refers to a composition which provides prolonged, sustained or extended release of the glatiramer acetate to the general systemic circulation of a subject or to local sites of action in a subject. This term may further refer to a composition which provides prolonged, sustained or extended duration of action (pharmacokinetics) of the glatiramer salt in a subject. In particular, the long acting pharmaceutical compositions provide a dosing regimen which ranges from once weekly to once every 6 months. According to currently preferable embodiments, the dosing regimen ranges from once a week, twice monthly (approximately once in every 2 weeks) to once monthly. Depending on the duration of action required, each depot or implantable device will typically contain between about 20 and 750 mg of the active ingredient, e.g., 40 mg or 80 mg, designed to be released over a period ranging from about 1 week to about 6 months, e.g., from about 2 weeks to about 1 month.

The present invention further provides a method of treating multiple sclerosis by parenteral administration of a long acting pharmaceutical composition comprising a therapeutically effective amount of glatiramer acetate to a subject in need thereof, wherein the pharmaceutical composition is prepared in accordance with the process of the present invention, and comprises reduced levels of organic solvent as described herein. The term "treating" as used herein refers to suppression or alleviation of symptoms after the onset of multiple sclerosis. Common symptoms after the onset of multiple sclerosis include, but are not limited to, reduced or loss of vision, stumbling and uneven gait, slurred speech, as well as urinary frequency and incontinence. In addition, multiple sclerosis can cause mood changes and depression, muscle spasms and severe paralysis. The "subject" to which the drug is administered is a mammal, preferably, but not limited to, a human. The term "multiple sclerosis" as used herein refers to an auto-immune disease of the central nervous system which is accompanied by one or more of the symptoms described hereinabove.

The present invention provides further provides a method of alleviating at least one symptom of relapsing-remitting multiple sclerosis (RRMS) in a patient suffering from RRMS, comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The present invention further provides, in another aspect, a method of increasing the tolerability of GA treatment in a human patient suffering from relapsing-remitting multiple sclerosis (RRMS), comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The present invention further provides, in another aspect, a method of reducing the frequency of relapses in a human patient suffering from relapsing-remitting multiple sclerosis (RRMS), comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The present invention further provides, in another aspect, a method of preventing or slowing progression of relapsing-remitting multiple sclerosis (RRMS) in a human patient suffering from RRMS, comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The depot compositions may further comprise one or more pharmaceutically acceptable excipient(s) selected from, but not limited to, co-surfactants, solvents/co-solvents, water-immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Suitable solvents/co-solvents include, but not limited to, alcohols, triacetin, dimethyl isosorbide, glycofurol, propylene carbonate, water, dimethyl acetamide, and the like or mixtures thereof. Suitable anti-foaming agents include, but are not limited to, silicon emulsions or sorbitan sesquioleate. Suitable stabilizers to prevent or reduce the deterioration of the components in the compositions include, but are not limited to, antioxidants such as glycine, α-tocopherol or ascorbate, BHA, BHT, and the like or mixtures thereof. Suitable tonicity modifiers include, but are not limited to, mannitol, sodium chloride, and glucose. Suitable buffering agents include, but are not limited to, acetates, phosphates, and citrates with suitable cations.

The depot systems encompass any forms known to a person of skill in the art. Suitable forms include, but are not limited to, biodegradable or non-biodegradable microspheres, implantable rods, implantable capsules, and implantable rings. Further contemplated are prolonged release gel depot and erodible matrices. Suitable implantable systems are described for example in US 2008/0063687, the content of which is hereby incorporated in its entirety. Implantable rods can be prepared as is known in the art using suitable micro-extruders.

In some embodiment, the long acting pharmaceutical compositions described herein provide equal or superior therapeutic efficacy to the commercially available daily injectable dosage forms, with reduced incidence of side effects and with reduced severity of side effects at the local and/or systemic level. In some embodiments, the compositions provide prolonged release or prolonged action of glatiramer in a subject as compared to a substantially similar dose of an immediate release formulation of glatiramer acetate.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: Preparation of PLGA Based Depot Microparticles of Glatiramer Acetate Containing Low Levels of Dichloromethane

TABLE 1

Raw materials and role

| Ingredient | Manufacturer | Role in Formulation | Composition [%] | Net Amount from Total Weight [g] |
|---|---|---|---|---|
| Sodium Chloride | SAFC | Creation of osmotic balance | 0.75 | 460 |
| Polyvinyl Alcohol | J. T. Baker | Surfactant | 0.45 | 275 |
| Dichloromethane (DCM) | Merck | Solvent of organic phase | 8.11 | 4,950 |
| Poly(Lactide-co-Glycolide) | Evonik | Polymer enclosing API | 0.90 | 550 |
| Water for Injection | B. Braun/Baxter | Solvent of internal and external phases | 89.69 | 54,745 |
| Glatiramer* Acetate | In house | API | 0.09 | 55 |

*Manufactured according to the process of U.S. Pat. No. 7,199,098.

Preparation Process (1) External water phase preparation: Partially hydrolyzed polyvinyl alcohol (PVA) solution at a concentration of 2% w/w in sterile WFI was prepared in a reactor and filtered through a 0.22 μm membrane. A solution of NaCl in sterile WFI was prepared and filtered through a 0.22 μm membrane into the reactor containing the PVA.

(2) [omitted]

(3) Organic phase preparation: Organic phase composed of dichloromethane and poly(lactide-co-glycolide) was prepared in a reactor and filtered through a 0.22 μm membrane.

(4) Internal water phase preparation: A solution containing sterile WFI and glatiramer acetate was prepared and filtered through a 0.22 μm membrane.

(5) Water-in-oil (w/o) emulsion preparation: Internal water phase was added to the organic phase and processed using IKA Ultra-Turrax T50 homogenizer equipped with a rotor stator dispersion device at 7,200 RPM for 10 minutes (high shear mixing).

(6) Water-in-oil-in-water (w/o/w) emulsion preparation: Water in oil emulsion (w/o) prepared in step 5 was added to half of the external water phase during continuing mixing of the w/o emulsion. The w/o/w double emulsion was processed using IKA Ultra-Turrax UTS80 homogenizer with a rotor stator head at 2,900 RPM for 3 minutes from the end of w/o transfer into the external water phase. Following, another 30 liters of the external water phase was added to the emulsion (quench).

(7) Solvent removal/evaporation: The w/o/w double emulsion formed in step (6) was mixed using the IKA UTS80 homogenizer at different speeds for 15-17 hours. Compressed air was bubbled at 0.5 Pa through the emulsion for 10-12 hours. Vacuum was applied for the portion of the process.

(8) Separation and washing: The suspension was centrifuged at 5,300 RPM for 10 minutes. The supernatant was discarded and the pellet (sedimented microparticles) is resuspended in 550 g WFI and mixed using a magnetic stirrer for 3 minutes. The resuspended microparticles were centrifuged at 2900 RPM for 10 minutes.

(9) Drying by Lyophilization: The washed microparticles were resuspended in about 750 g sterile WFI and are kept at −20° C. until lyophilization. Lyophilization was carried out using sterile lyoguard trays as follows: Freeze at −40° C., 24 hours. Primary drying at 0.2 hPa, −5° C., 48 hours. Secondary drying at 0.2 hPa, 10° C., 48 hours.

The dry GA depot composition is provided Table 2:

TABLE 2

GA Depot 40 mg Composition per Vial

| Ingredient | mg/vial# | Function |
|---|---|---|
| GA | 44 | Active |
| POLYGLACTIN 50:50, molecular weight 7,000-17,000 (PLGA) | 506 | Carrier |
| Water for Injection* | — | Compounding solvent |
| Dichloromethane (DCM)* | — | Compounding solvent |
| Polyvinylalcohol** | — | surfactant |
| NaCl** | — | Isotonic pressure |

*Evaporated during lyophilization process
**Removed during production, does not incorporate into final product
Each vial contain 10% overage to compensate for losses during withdrawal of the reconstituted product A summary of the procedure, equipment and materials involved in the preparation of GA Depot 55 g using the 100 L reactor system is depicted in Table 3:

TABLE 3

| Stage | Composition | Vessels and Instruments |
|---|---|---|
| External Water Phase | 13750 g PVA 2% solution<br>460 g NaCl<br>40845 g WFI | 30 L glass reactor filtered through 0.2 μm aqueous membrane. |
| Internal water phase | 55 g GA (absent in placebo)<br>425 g WFI | 2 L glass bottle filtered through 0.2 μm aqueous membrane. |
| Organic phase | 550 g PLGA<br>4950 g DCM | 10 L glass reactor filtered through 0.2 μm organic membrane. |
| Water in oil emulsification | Internal water phase is added to organic phase and processed at 7200 RPM for 10 minutes | Homogenized in 10 L SS reactor using IKA Ultra-Turrax T50 homogenizer. |
| Water in oil in water emulsification | Water in oil emulsion is added to external water phase and processed at 2900 RPM for 3 minutes. | Homogenized in 100 L SS reactor using IKA Ultra-Turrax UTS80 homogenizer. |
| Evaporation of DCM | Mixing of double emulsion and bubbling of compressed air overnight followed by vacuum for 5 hours | Evaporation in 100 L SS reactor using IKA Ultra-Turrax UTS80 homogenizer. |
| Separation and washing | Centrifugation at 5300 RPM and 2900 RPM for 10 minutes. | Thermo Fisher Scientific RC 12BP+ centrifuge |
| Re-suspension | Dispersion of precipitate with 550 g WFI | NA |

Results and Discussion

DCM residual content: Table 4 details evaporation speed, duration of vacuum application, and DCM residual content of eight batches prepared. The results show that DCM residual content in the final formulation of GA Depot decreases by increasing evaporation speed and time of vacuum. Residual DCM complied with the limits at a speed of 2,750 RPM and 5 hours of vacuum as implemented in placebo batch (6). Two additional batches, (7, placebo)) and (8 (glatiramer acetate)) were prepared under the same evaporation conditions in order to ensure reproducibility.

TABLE 4

| Product | Batch No. | Evaporation Speed [RPM] | Pressure of Compressed Air [bar] | Time of Vacuum [hr] | DCM Residual Content [ppm] |
|---|---|---|---|---|---|
| Placebo for GA Depot 55 g | (1) | 900 | 0.5 | Vacuum was not applied | 5761 |
|  | (2) | 800 |  |  | NA |
|  | (3) | 2100 |  |  | 3872 |
|  | (4) | 2216 |  |  | 1921 |
|  | (5) | 2500 |  | 3 | 945 |
|  | (6) | 2750 |  | 5 | 213 |
|  | (7) | 2750 |  | 5 | 82 |
| GA Depot 55 g | (8) | 2750 |  | 5 | 92 |

Sterility and bacterial endotoxins: The first four placebo batches were not prepared aseptically and hence sterility and bacterial endotoxin data are not relevant. The subsequent batches were proven sterile and fall within bacterial endotoxin limitation as can be seen in Table 5 below.

TABLE 5

| Product | Batch No. | Sterility | Bacterial Endotoxins ≤ 0.3 EU/mg |
|---|---|---|---|
| Placebo for GA Depot 55 g | (1) | Not Applicable | Not Applicable |
|  | (2) |  |  |
|  | (3) |  |  |
|  | (4) |  |  |
|  | (5) | No growth | <0.05 |
|  | (6) | No growth | 0.1904 |
|  | (7) | No growth | <0.05 |
| GA Depot 55 g | (8) | No growth | 0.1303 |

In Vitro Release Profile

The in vitro system is as described in U.S. Pat. Nos. 8,377,885 and 8,796,226 as summarized below:

Materials and Methods

Equipment
  20 ml vials
  multi-point magnetic stirrer
  Incubator
  Pipettors
  UV-Vis spectrophotometer Shimadzu 1601
  Reagents and plastic/glassware
  Test-articles: Dry lyophilized microparticles containing glatiramer acetate made by the process of the invention (batch 9) or according to the process of U.S. Pat. Nos. 8,377,885 and 8,796,226 (batch 10).
  Temperature: 37° C.
  2,4,6-trinitrobenzenesulfonic acid (TNBS, picrylsulfonic acid, 170.5 mM) 5% in MeOH Process description: 20 ml of PBS (0.01M phosphate, 0.05% $NaN_3$) pH 7.4 were added to each vial. The vials were placed at 37° C. and stirred with a small magnet. 600 μl samples were centrifuged at 10,000 g for 5 minutes. 500 μl of supernatant were transferred to a 1.5 ml microtube followed by the addition of 500 μl of 0.1M borate buffer (2-fold dilution) and 50 μl TNBS. The resulting composition was mixed and was kept on the bench for 30 minutes. Analysis was performed using TNBS method (described below).

The remaining precipitated particles, re-suspended with 500 μl of fresh PBS (with $NaN_3$), were returned to the vial. Correct calculation for released amount of glatiramer acetate was performed in a further release process for 2.5% for each time-point.

The release of the incorporated glatiramer acetate was carried out in tightly closed 20 ml glass vials, using incubator at 37° C., equipped with a multi-point magnetic stirrer. Phosphate buffered saline (PBS) with pH 7.4 was used as a release media.

The release of the glatiramer acetate was tested over a period of 1-30 days. The content of GA released is determined by a GPC method
  Instrument: Suitable HPLC system equipped with a UV detector
  Column: Superose 12 HR 10/30 column
  Detection: UV at 208 nm
  Flow rate: 0.5 ml/min
  Injection volume: 10 μL
  Column temperature: ambient
  Mobile phase: 0.2M phosphate buffer pH 1.5

A representative release profile of two representative samples of GA depot made by the process of the invention are provided in Table 6.

TABLE 6

Release profile of 100L GA Depot, two representative batches, batch (9) made by the process of the invention, in comparison to batch (10) according to the process described in U.S. Pat. No. 8,377,885 and U.S. Pat. No. 8,796,226.

| Batch number | 9 | 10 |
|---|---|---|
| day 0 | 11% | NT |
| day 1 | 13% | 10% |
| day 7 | 19% | 22% |
| day 14 | 43% | 35% |
| day 21 | 80% | 68% |
| day 30 | 98% | 93% |

Conclusions

As demonstrated herein, it can be concluded that by increasing evaporation speed followed by the application of vacuum it was possible to optimize DCM evaporation and acquire results which fall within the required specifications. The results show that the optimal evaporation conditions are a homogenization speed of about 2,750 RPM and about 5 hours of vacuum. Surprisingly, minimization of DCM levels was achievable utilizing the process of the invention, while still maintaining the desired product attributes (GA binding percentage, particle morphology and release profile of the glatiramer acetate active ingredient remained intact despite the process modifications).

Furthermore, the batches were tested for bacterial endotoxins and sterility, which also conformed to their acceptance criteria.

Example 2: Comparative Experiment

GA Depot was prepared according to the process described in Example 3 of WO 2011/080733 (corresponding to U.S. Pat. Nos. 8,377,885 and 8,796,226). For solvent (DCM) removal, an open beaker containing the double emulsion was placed on a magnetic plate stirrer and stirred for 3-4 hours at room temperature in a fume hood until all solvent evaporated and the microparticles had solidified. No air stream and/or vacuum was applied.

Lyophilized samples were tested for DCM levels using headspace GC. Average amount of DCM detected in the samples was 19,453 ppm.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method of alleviating at least one symptom of relapsing-remitting multiple sclerosis (RRMS) in a patient suffering from RRMS, comprising administering to the patient a long acting parenteral pharmaceutical composition in sustained release depot form comprising 40 mg glatiramer acetate at a dosing schedule of once every 2 weeks to once monthly, wherein the pharmaceutical composition is prepared by a process comprising the steps of:
   a. preparing an internal aqueous phase comprising glatiramer acetate and water;
   b. preparing an organic phase comprising a biodegradable or non-biodegradable polymer and a water-immiscible volatile organic solvent;
   c. preparing an external aqueous phase comprising water and a surfactant;
   d. mixing the internal aqueous phase obtained in step (a) and the organic phase obtained in step (b) to form a water-in-oil (w/o) emulsion;
   e. mixing the water-in-oil (w/o) emulsion obtained in step (d) with the external water phase obtained in step (c) to obtain a water-in-oil-in-water (w/o/w) double emulsion;
   f. removing the organic solvent by mixing the water-in-oil-in-water (w/o/w) double emulsion obtained in step (e), and applying a compressed air stream and a vacuum, wherein the compressed air stream is applied at a pressure of about 0.1 to 1 bar, and wherein the vacuum is applied for at least about 3 hours; and
   g. drying to obtain microparticles of glatiramer acetate, said microparticles comprising less than about 1,000 ppm of residual organic solvent.

2. The method according to claim 1, wherein the water-immiscible volatile organic solvent is a halogenated organic solvent selected from the group consisting of dichloromethane (DCM) and chloroform.

3. The method according to claim 1, wherein the process further comprises the step of filtering or centrifuging the product of step (f) and optionally washing with water prior to the drying step (g).

4. The method according to claim 1, wherein the biodegradable or non-biodegradable polymer is selected from the group consisting of poly(D,L, lactic acid) (PLA), polyglycolides (PGA), poly(lactide-co-glycolide) (PLGA), polycaprolactone, polyhydroxybutyrate, polyorthoesters, polyalkaneanhydrides, gelatin, collagen, oxidized cellulose, and polyphosphazene.

5. The method according to claim 4, wherein the biodegradable polymer is poly(lactide-co-glycolide) (PLGA).

6. The method according to claim 1, wherein the surfactant is selected from polyvinyl alcohol (PVA), partially hydrolyzed polyvinyl alcohol (PVA), polysorbate, polyethylene oxide-polypropylene oxide block copolymers and cellulose esters.

7. The method according to claim 6, wherein the surfactant is PVA or partially hydrolyzed PVA.

8. The method according to claim 1, wherein administering comprises subcutaneous or intramuscular implantation at a medically acceptable location.

9. The method according to claim 1, wherein alleviating at least one symptom of relapsing-remitting multiple sclerosis (RRMS) comprises reducing the frequency of relapses.

10. A method of alleviating at least one symptom of relapsing-remitting multiple sclerosis (RRMS) in a patient suffering from RRMS, comprising administering to the patient a long acting parenteral pharmaceutical composition in sustained release depot form comprising 40 mg glatiramer acetate at a dosing schedule of once every 2 weeks to once monthly, wherein the pharmaceutical composition comprises less than about 1,000 ppm of residual organic solvent and is prepared by a process comprising a water-in oil-in water (w/o/w) double emulsification.

11. The method according to claim 10, wherein the organic solvent is a halogenated organic solvent selected from the group consisting of dichloromethane (DCM) and chloroform.

12. The method according to claim 10, wherein the pharmaceutical composition comprises a biodegradable or non-biodegradable polymer selected from the group consisting of poly(D,L, lactic acid) (PLA), polyglycolides (PGA), poly(lactide-co-glycolide) (PLGA), polycaprolactone, polyhydroxybutyrate, polyorthoesters, polyalkaneanhydrides, gelatin, collagen, oxidized cellulose, and polyphosphazene.

13. The method according to claim 12, wherein the biodegradable polymer is poly(lactide-co-glycolide) (PLGA).

14. The method according to claim 10, wherein administering comprises subcutaneous or intramuscular implantation at a medically acceptable location.

15. The method according to claim 10, wherein alleviating at least one symptom of relapsing-remitting multiple sclerosis (RRMS) comprises reducing the frequency of relapses.

16. The method according to claim 10, wherein alleviating at least one symptom of relapsing-remitting multiple sclerosis (RRMS) comprises preventing or slowing the progression of RRMS.

17. A method of treating a human patient suffering from relapsing-remitting multiple sclerosis (RRMS), comprising administering to the patient a long acting parenteral pharmaceutical composition comprising 40 mg glatiramer acetate and poly(lactide-co-glycolide) (PLGA) at a dosing schedule of once every 2 weeks to once monthly, wherein the pharmaceutical composition comprises less than about 1,000 ppm of residual organic solvent and is prepared in the form of a sustained release depot comprising microparticles of glatiramer acetate.

18. The method according to claim 17, wherein treating a human patient suffering from RRMS comprises reducing the frequency of relapses.

19. The method according to claim 17, wherein administering comprises subcutaneous or intramuscular implantation at a medically acceptable location.

20. The method according to claim 17, wherein the long acting parenteral pharmaceutical composition is prepared by a process comprising the steps of:
a. preparing an internal aqueous phase comprising glatiramer acetate and water;
b. preparing an organic phase comprising poly(lactide-co-glycolide) (PLGA) and a water-immiscible volatile organic solvent;
c. preparing an external aqueous phase comprising water and a surfactant;
d. mixing the internal aqueous phase obtained in step (a) and the organic phase obtained in step (b) to form a water-in-oil (w/o) emulsion;
e. mixing the water-in-oil (w/o) emulsion obtained in step (d) with the external water phase obtained in step (c) to obtain a water-in-oil-in-water (w/o/w) double emulsion;
f. removing the organic solvent by mixing the water-in-oil-in-water (w/o/w) double emulsion obtained in step (e), and applying a compressed air stream and a vacuum; and
g. drying to obtain microparticles of glatiramer acetate.

* * * * *